United States Patent
Doi et al.

(10) Patent No.: US 7,195,894 B2
(45) Date of Patent: Mar. 27, 2007

(54) MKK7 ACTIVATION INHIBITOR

(75) Inventors: Hirofumi Doi, Chiba (JP); Shinya Hosogi, Chiba (JP); Naoya Wada, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 26 days.

(21) Appl. No.: 10/519,465

(22) PCT Filed: Jun. 27, 2003

(86) PCT No.: PCT/JP03/08179

§ 371 (c)(1),
(2), (4) Date: Feb. 9, 2005

(87) PCT Pub. No.: WO2004/002532

PCT Pub. Date: Jan. 8, 2004

(65) Prior Publication Data

US 2006/0172360 A1    Aug. 3, 2006

(30) Foreign Application Priority Data

Jun. 28, 2002   (JP)   ............................. 2002-190909
Jun. 28, 2002   (JP)   ............................. 2002-190910

(51) Int. Cl.
*C12N 15/09* (2006.01)
(52) U.S. Cl. ....................... 435/69.2; 435/17
(58) Field of Classification Search .................... None
See application file for complete search history.

(56) References Cited

U.S. PATENT DOCUMENTS 6,465,618 B1   10/2002   Nishida et al. ............. 530/350
2004/0121398 A1   6/2004   Doi et al. ..................... 435/7.1

OTHER PUBLICATIONS

Xie et al., "Crystal structure of JNK3: a kinase implicated in neuronal apoptosis," *Structure*, 1998, vol. 6, No. 8, pp. 983-991.
Ikeda et al., "Mixed lineage kinase LZK forms a functional signaling complex with JIP-1, a scaffold protein of the c Jun $NH_2$-Therminal kinase pathway," *Journal of Biochemistry*, 2001 No. 130, pp. 773-781.
Yamauchi et al., "Differential regulation of mitogen-activated protein kinase kinase 4 (MKK4) and 7 (MKK7) by signaling from G protein β γ sub-unit in human embroyonal kidney 293 cells," *The Journal of Biological Chemistry*, 1999, No. 274, vol. 4, pp. 1957-1965.
Yao et al., Activation of stress-activated protein kinases/c-Jun n-terminal protein kinases (SAPKs/JNKs) by a novel mitogen-activated protein kinase kinase (MKK7), *The Journal of Biological Chemistry*, 1997, vol. 272, No. 51, pp. 32378-32383.
Tournier et al., "The MKK7 gene encodes a group of c-Jun NH2-Terminal kinase kinases," *Molecular and Cellular Biology*, 1999, vol. 19, No. 2, pp. 1569-1581.

Chen et al., "Mammalian c-Jun N-terminal kinase pathway and STE20-related kinases," *Gene Therapy and Molecular Biology*, 1999, vol. 4, pp. 83-98.
Dan et al., "The Ste20 group kinases as regulators of MAP kinase cascades," *Trends in Cell Biology*, 2001, vol. 11, No. 5, pp. 220-230.
Eilers et al., "Role of the Jun kinase pathway in the regulation of c-Jun Expression and Apoptosis in Sympathetic Neurons," *J. Neurosci.*, 1998, vol. 18, No. 5, pp. 1713-1724.
Ham et al., "A c-Jun dominant negative mutant protects sympathetic neurons against programmed cell death," *Neuron*, 1995, vol. 14, pp. 927-939.
Yang et al., "Absence of excitotoxicity-induced apoptosis in the hippocampus of mice lacking the Jnk3 gene," *Nature*, 1997, vol. 389, pp. 865-870.
Moriguchi et al., "A novel SAPK/JNK kinase, MKK7, stimulated by TNFα and cellular stresses," *Embo. J.*, 1997, vol. 16, No. 23, pp. 7045-7053.
Foltz et al., "Human mitogen-activated protein kinase kinase 7 (MKK7) is a highly conserved c-Jun N-terminal kinase/stress-activated protein kinase (JNK/SAPK) activated by environmental stresses and physiological stimuli," *J. Biol. Chem.*, 1998, vol. 273, No. 15, pp. 9344-9351.
Yang et al., "Targeted disruption of the MKK4 gene causes embryonic death, inhibition of c-Jun NH2-terminal kinase activation, and defects in AP-1 transcriptional activity," *Proc. Natl. Acad. Sci. U.S.A.*, 1997, vol. 94, No. 7, pp. 3004-3009.
Bagrodia et al., "Cdc42 and PAK-mediated signaling leads to jun kinase and p38 mitogen-activated protein kinase activation," *J. Biol. Chem.*, 1995, vol. 270, No. 47, pp. 27995-27998.
Brown et al., "Human Ste20 homologue hPAK1 links GTPases to the JNK MAP kinase pathway," *Curr. Biol.*, 1996, vol. 6, No. 5, pp. 598-605.

(Continued)

*Primary Examiner*—Ralph Gitomer
*Assistant Examiner*—Bin Shen
(74) *Attorney, Agent, or Firm*—Kilyk & Bowersox, P.L.L.C.

(57) ABSTRACT

PAK4 and JIK, both of which bind to MKK7 and directly phosphorylate MKK7, were found in the present invention. The present invention provides an inhibitor of c-Jun phosphorylation caused by JNK3 and a method for inhibiting the same, and an agent for preventing and/or treating a disorder attributable to c-Jun phosphorylation caused by JNK3 and a method for preventing and/or treating the same, all of which comprise inhibiting one member selected from the following: the binding of PAK4 to MKK7, the phosphorylation of MKK7 by PAK4, the binding of JIK to MKK7, and the phosphorylation of MKK7 by JIK. Further, the present invention provides a method for identifying a compound that inhibits the binding of PAK4 to MKK7, the phosphorylation of MKK7 caused by PAK4, the binding of JIK to MKK7, or the phosphorylation of MKK7 caused by JIK, as well as the compound obtained thereby. Furthermore, the present invention provides a pharmaceutical composition containing an effective amount of at least one member selected from the group consisting of the aforementioned compound and the aforementioned inhibitor.

1 Claim, 6 Drawing Sheets

OTHER PUBLICATIONS

Frost, et al., "Actions of Rho family small G proteins and P21-activated protein kinases on mitogen-activated protein kinase family members," *Mol. Cell. Biol.*, 1996, vol. 16, No. 7, pp. 3707-3713.

Abo et al., "PAK4, a novel effector for Cdc42Hs, is implicated in the reorganization of the actin cytoskeleton and in the formation of filopodia," *Embo J.*, 1998, vol. 17, No. 22, pp. 6527-6540.

Bazenet et al., "The small GTP-binding protein Cdc42 is required for nerve growth factor withdrawal-induced neuronal death," *Proc. Natl. Acad. Sci. U.S.A.*, 1998, vol. 95, pp. 3984-3989.

Urano et al., "IRE1 and efferent signaling from the endoplasmic reticulum," *J. Cell Sci.*, 2000, vol. 113, pp. 3697-3702.

Urano et al., "Coupling of stress in the ER to Activation of JNK protein kinases by transmembrane protein kinase IRE1," *Science*, 2000, vol. 287, pp. 664-666.

Yoneda et al., "Activation of caspase-12, an endoplastic reticulum (ER) resident caspase, through tumor necrosis factor receptor-associated factor 2-dependent mechanism in response to the ER stress," *J. Biol. Chem.*, 2001, vol. 276, No. 17, pp. 13935-13940.

Tassi et al., "Human JIK, a novel member of the STE20 kinase family that inhibits JNK and is negatively regulated by epidermal growth factor," *J. Biol. Chem.*, 1999, vol. 274, No. 47, pp. 33287-33295.

Zhang et al., "Cloning of DPK, a novel dendritic cell-derived protein kinase activating the ERK1/ERK2 and JNK/SAPK pathways," *Biochem. Biophys. Res. Commun.*, 2000, vol. 274, pp. 872-879.

Zhang et al., "Activation of JNK and transcriptional repressor ATF3/LRF1 through the IRE1/TRAF2 pathway is implicated in human vascular endothelial cell death by homocysteine," *Biochem. Biophys. Res. Commun.*, 2001, vol. 289, pp. 718-724.

*Cell Technologies*, 2001, vol. 20, No. 11. (with partial English translation).

International Preliminary Examination Report for PCT/JP2003/008179 (English translation).

Fig. 1

Score = 57.7
```
299 YDIRADVWSLGISLVELATGQFPY      (SEQ ID NO: 9)
492 YGPEVDIWSLGIMVIEMVDGEPPY      (SEQ ID NO: 10)
    Y   D WSLGI   E   G PY
         (SEQ ID NO: 11)
```
Score = 45.3
```
120 LENLGEMGSGTCGQVWKMRFRKTGHVIAVKQM  (SEQ ID NO: 12)
321 LDNFIKIGEGSTGIVCIATVRSSGKLVAVKKM  (SEQ ID NO: 13)
    L N   G G G V    R G   AVK M
```

Score = 37.0
```
 65 PTPPARPRHMLGLP                (SEQ ID NO: 14)
105 PPPPARARQENGMP                (SEQ ID NO: 15)
     P PPAR R   G P
         (SEQ ID NO: 16)
```
Score = 31.4
```
361 LTKDHRKRPKYNKLLEHSFIKR        (SEQ ID NO: 17)
553 LVRDPAQRATAAELLKHPFLAK        (SEQ ID NO: 18)
    L  D  R     LL H F
```

Score = 30.9
```
169 VVLKSHDCPYIVQCFGTFITNTDVFIAMELM   (SEQ ID NO: 19)
368 VIMRDYQHENVVEMYNSYLVGDELWVVMEFL   (SEQ ID NO: 20)
    V           V              ME
```

Score = 27.0
```
 33 DISPQRPRPT-LQLPLANDGGSRSPSSESSPQHP (SEQ ID NO: 21)
226 DVAPNGPSAGGLAIPQSSSSSSRPPTRARGAPSP (SEQ ID NO: 22)
    D   P  P   L P      SR P       P
```

Score = 27.9
```
 58 SESSPQHPTPPARPR               (SEQ ID NO: 23)
240 PQSSSSSSRPPTRAR               (SEQ ID NO: 24)
       SS     PP R R
```

Score = 26.9
```
 51 GGSRSPSSESSPQHPTPPAR          (SEQ ID NO: 25)
235 GGLAIPQSSSSSSRPPTRAR          (SEQ ID NO: 26)
    GG   P S SS      P  AR
```

Score = 25.1
```
 34 ISPQRPRPTLQLPLANDGGSRS        (SEQ ID NO: 27)
299 VSHEQFRAALQL-VVDPGDPRS        (SEQ ID NO: 28)
      S   R  LQL    G  RS
```

Fig. 5

```
Score =  59.6
    299  YDIRADVWSLGISLVELA                  (SEQ ID NO: 29)
    198  YDGKVDIWSLGITCIELA                  (SEQ ID NO: 30)
         YD   D WSLGI   ELA
                 (SEQ ID NO: 11)
Score =  39.0
    123  LGEMGSGTCGQVWKMRFRKTGHVIAVKQMRRSGNK  (SEQ ID NO: 31)
     27  LHEIGHGSFGAVYFATNAHTSEVVAIKKMSYSGKQ  (SEQ ID NO: 32)
         L E GG  GV        T  V AK M  SG Score =  30.1
      7  EQKLSRLEAKLKQENREARRRI               (SEQ ID NO: 33)
    472  QKQLIALENKLKAEMDEHRLKL               (SEQ ID NO: 34)
           L   LE KLK E   E R Score =  28.9
     91  EIDQKLQEIMKQTGYL                     (SEQ ID NO: 35)
     61  QTHEKWQDILKEVKFL                     (SEQ ID NO: 36)
               K Q I K     L Score =  29.3
    102  QTGYLTIGGQRYQAEINDL                  (SEQ ID NO: 37)
    761  QTRKLAILAEQYEQSINEM                  (SEQ ID NO: 38)
         QT   L I   Y     IN Score =  25.7
      6  LEQKLSRLEAKLKQENRE                   (SEQ ID NO: 39)
    831  LEQRVSLRRAHLEQKIEE                   (SEQ ID NO: 40)
         LEQ  S    A L Q   E Score =  26.4
    111  QRYQAEINDLENL                        (SEQ ID NO: 41)
    291  QRTKDAVRELDNL                        (SEQ ID NO: 42)
         QR         L NL Score =  26.3
    201  TCAEKLKKRM                           (SEQ ID NO: 43)
    558  ICKEKIKEEM                           (SEQ ID NO: 44)
          C EK K   M Score =  26.7
    236  KHGVIHRDVKPSNILLD                    (SEQ ID NO: 45)
    273  RHDFVRRD-RPLRVLID                    (SEQ ID NO: 46)
            H   RD  P   L D
```

MKK7 ACTIVATION INHIBITOR

This application is filed under rule 371 claiming priority to PCT Application PCT/JP03/08179 filed Jun. 27, 2003, which claims priority to both JAPAN 2002-190909 filed Jun. 28, 2002 and JAPAN 2002-190910 filed Jun. 28, 2002.

TECHNICAL FIELD

The present invention relates to the inhibition of c-Jun phosphorylation caused by c-Jun N-terminal kinase 3 (JNK3), comprising inhibiting the activation of MAP kinase kinase 7 (MKK7), and to the improvement of a disorder attributable to c-Jun phosphorylation by JNK3, as well as to improvement of a neurodegenerative disorder. More particularly, the present invention relates to an inhibitor of c-Jun phosphorylation caused by JNK3 and a method for inhibiting the same, comprising inhibiting the interaction of MKK7 with p21-activated kinase 4 (PAK4) and/or the interaction of MKK7 with JNK/SAPK-inhibitory kinase (JIK), that is, inhibiting the MKK7 activation that results from the binding of PAK4 to MKK7 followed by direct phosphorylation of MKK7 by PAK4 and/or that results from the binding of JIK to MKK7 followed by direct phosphorylation of MKK7 by JIK. The present invention relates further to a preventive agent and/or an inhibitor of a disorder attributable to c-Jun phosphorylation by JNK3, and a method for preventing and/or inhibiting the same, as well as to a preventive agent and/or an inhibitor of neurodegeneration, and a method for preventing and/or inhibiting the same, all of which has the aforementioned features. The present invention relates still further to a method for identifying a compound that inhibits the binding of PAK4 to MKK7, the phosphorylation of MKK7 by PAK4, the binding of JIK to MKK7, or the phosphorylation of MKK7 by JIK, and to a compound that is obtained by the identification method.

BACKGROUND ART c-Jun N-terminal kinase (hereinafter abbreviated as JNK) is a protein kinase that belongs to the MAP kinase (hereinafter abbreviated as MAPK) family. Three JNK genes (JNK1, JNK2 and JNK3) have been discovered in mammals. Among these, JNK3 is selectively expressed, for example, in the brain-nervous system.

Unlike the classical MAPK, JNK3 is barely activated by proliferation stimuli. The activation of JNK3 is caused by stress on a cell (e.g., DNA damage, ultraviolet radiation, heat, high osmotic pressure, endoplasmic reticulum stress, active oxygen) or by an inflammatory cytokine (e.g., tumor necrosis factor (TNF), interleukin-1 (IL-1)). The activated JNK is understood to translocate from the cytoplasm into the nucleus and control the expression of target genes via the phosphorylation of transcription factors, such as c-Jun.

The activation of JNK is involved in apoptosis induced by various stress stimuli. For example, it has been reported that JNK is activated in nerve cell death resulting from withdrawal of nerve growth factor (NGF, non-patent document 1), and that nerve cell death resulting from withdrawal of NGF is suppressed by expression of a dominant negative c-Jun mutant (non-patent document 2). In addition, it has been reported that excitatory neuron death induced by administration of kainic acid is suppressed in a JNK3 knock-out mouse (non-patent document 3). The above findings suggest that the activation of JNK3 is involved in nerve cell death.

MKK4 and MKK7, which are members of the MAPK kinase family (hereinafter abbreviated as MAPKK), are known to activate JNK. MKK7 is also called MAPKK7, MAP2K7 and JNKK2, and specifically phosphorylates and activates JNK (non-patent document 4 and 5). In contrast, MKK4 phosphorylates and activates JNK as well as phosphorylates and activates ERK2 and p38, which are also members of MAPK family. Since JNK activation by osmotic pressure stimulus or ultraviolet radiation is still observed in an embryonic stem cell (ES cell) with a disrupted MKK4 gene (non-patent document 6), MKK7 is considered to work on the activation of JNK independently of MKK4.

The activation of JNK is also caused by a signal from cdc42, which is one of the low-molecular weight GTP proteins (non-patent document 7). PAK (p21-activated kinase) is known to be a kinase that binds to cdc42 and transmits a signal from cdc42. Actually, it has been reported that the JNK signaling pathway is activated by over-expression of PAK1, PAK2, PAK3 or PAK4, all of which are members of the PAK family (non-patent document 8, 9, 7 and 10, respectively). However, the detailed mechanism of the signaling pathway between PAK and the JNK activation has not yet become clear. For example, whether the signaling is direct or indirect is not clear.

There have been some reports suggesting the involvement of cdc42 in nerve cell death. For example, forced expression of activated cdc42 in nerve cells induces nerve cell death, whereas a dominant negative cdc42 mutant suppresses nerve cell death resulting from withdrawal of NGF (non-patent document 11). In addition, it is reported that activated cdc42 activates MKK7 as well as activates JNK (non-patent document 12). Therefore, the signaling pathway from cdc42 to JNK, which is mediated by MKK7, may be possibly involved in nerve cell death.

Endoplasmic reticulum stress (hereinafter abbreviated as ER stress) is among the stresses causing the activation of JNK3. ER stress is caused by the accumulation of abnormal proteins in the endoplasmic reticulum (hereinafter may be abbreviated as ER) as a result of a defect in the protein folding process in the ER due to various stimuli (e.g., glucose exhaustion, change in homeostasis of calcium concentration, active enzyme). When ER stress occurs, expression of endoplasmic reticulum molecular chaperon is induced (that is, unfolded protein response: UPR), thus eliminating the misfolding. IRE1 is known to work in this process as an ER stress sensor protein (non-patent document 13).

It has been reported that IRE1 and TRAF2 are involved in the process of JNK activation caused by ER stress (non-patent document 14 and 15). Concretely, the IRE1 disrupted cell line shows suppressed JNK activation in response to ER stress, whereas over-expression of IRE1 activates JNK. In addition, IRE1 binds to TRAF2, and a dominant negative TRAF2 mutant suppresses the JNK activation by IRE1.

In addition to the above, JIK (also referred to as DPK) is also known as a protein that is involved in the process of JNK activation by ER stress. It is considered that JIK binds to IRE1 and TRAF2, and is involved in the JNK activation by ER stress. For example, over-expression of JIK augments the JNK activation by ER stress, whereas an active-site-deletion mutant of JIK suppresses the JNK activation by ER stress (non-patent document 15).

JIK is one of the STE20-related serine/threonine kinases that are human homologs of yeast Ste20p protein. In addition to the aforementioned actions of JIK, it has been reported that JIK inhibits the JNK activation by epidermal growth factor (EGF) stimulus, while the activity of JIK itself is suppressed (non-patent document 16), and that the overexpression of JIK leads to the JNK activation (non-patent document 17).

On the other hand, overload of ER stress is known to induce apoptosis. Since ischemia or accumulation of an abnormal protein such as polyglutamine or amyloid β (hereinafter abbreviated as Aβ) possibly gives rise to ER stress, it is pointed out that there is a relationship between nerve cell death due to ER stress and a neurodegenerative disorder.

Since apoptosis induced by ER stress was suppressed by each dominant negative mutant of MKK4 and MKK7 (non-patent document 18), JNK activation via MKK4 or MKK7 is likely to be involved in the apoptosis induced by ER stress.

The literature cited in the present specification is listed below.

Patent document 1: International Patent Publication WO 01/67299.
Non-patent document 1: Eilers A. et al., J. Neurosci., 1998, Vol. 18, pp. 1713–1724.
Non-patent document 2: Ham J. et al., Neuron, 1995, Vol. 14, pp. 927–939.
Non-patent document 3: Yang D. et al., Nature, 1997, Vol. 389, pp. 865–870.
Non-patent document 4: Moriguchi T. et al., EMBO J., 1997, Vol. 16, pp. 7045–7053.
Non-patent document 5: Foltz I. et al., J. Biol. Chem., 1998, Vol. 273, pp. 9344–9351.
Non-patent document 6: Yang D. et al., Proc. Natl. Acad. Sci. U.S.A., 1997, Vol. 94, pp. 3004–3009.
Non-patent document 7: Bagrodia S. et al., J. Biol. Chem., 1995, Vol. 270, pp. 27995–27998.
Non-patent document 8: Brown J. et al., Curr. Biol., 1996 Vol. 6, pp. 598–605.
Non-patent document 9: Frost J. et al., Mol. Cell. Biol., 1996, Vol. 16, pp. 3707–3713.
Non-patent document 10: Abo A. et al., EMBO J., 1998, Vol. 17, pp. 6527–6540.
Non-patent document 11: Bazenet C. et al., Proc. Natl. Acad. Sci. U.S.A., 1998, Vol. 95, pp. 3984–3989.
Non-patent document 12: Foltz I. et al., J. Biol. Chem., 1998, Vol. 273, pp. 9344–9351.
Non-patent document 13: Urano F. et al., J. Cell Sci., 2000, Vol. 113, pp. 3697–3702.
Non-patent document 14: Urano F. et al., Science, 2000, Vol. 287, pp. 664–666.
Non-patent document 15: Yoneda T. et al., J. Biol. Chem., 2001, Vol. 276, pp. 13935–13940.
Non-patent document 16: Tassi E. et al., J. Biol. Chem., 1999, Vol. 274, pp. 33287–33295.
Non-patent document 17: Zhang W. et al., Biochem. Biophys. Res. Commun., 2000, Vol. 274, pp. 872–879.
Non-patent document 18: Zhang C. et al., Biochem. Biophys. Res. Commun., 2001, Vol. 289, pp. 718–724.
Non-patent document 19: Cell Technology, 2001, Vol. 20, No. 11, Feature Story: The mechanism of onset of neurodegenerative disorders and the perspective of treatment thereof.

DISCLOSURE OF THE INVENTION

In view of the current situation described above, to inhibit any one of the stages in the mechanism of JNK activation by various stresses makes it possible to more clearly understand a disorder attributable to apoptosis induced by the JNK activation, such as, more specifically, a neurodegenerative disorder, as well as to prevent and/or treat such a disorder.

For example, discovery of a protein capable of interacting with MKK7 and inhibiting the MKK7 activation would make it possible to inhibit the JNK activation.

The present inventors made an in-silico prediction of the interaction of MKK7 with PAK4 or JIK, and proved the interaction experimentally, and further discovered that the interaction leads to the phosphorylation of MKK7 by PAK4 or JIK followed by the activation of the JNK3 signaling pathway, all of which discoveries contribute to the achievement of the present invention.

More specifically, the first aspect of the present invention relates to an inhibitor of c-Jun phosphorylation by c-Jun N-terminal kinase 3, having at least one function selected from the group consisting of the following functions:
  i) inhibiting the binding of p21-activated kinase 4 (PAK4) to MAP kinase kinase 7 (MKK7);
  ii) inhibiting the phosphorylation of MKK7 caused by PAK4;
  iii) inhibiting the binding of JNK/SAPK-inhibitory kinase (JIK) to MAP kinase kinase 7 (MKK7); and
  iv) inhibiting the phosphorylation of MKK7 caused by JIK.

Another aspect of the present invention relates to a method for inhibiting c-Jun phosphorylation caused by c-Jun N-terminal kinase 3, comprising at least one step selected from the group consisting of the following steps:
  i) inhibiting the binding of p21-activated kinase 4 (PAK4) to MAP kinase kinase 7 (MKK7);
  ii) inhibiting the phosphorylation of MKK7 caused by PAK4;
  iii) inhibiting the binding of JNK/SAPK-inhibitory kinase (JIK) to MAP kinase kinase 7 (MKK7); and
  iv) inhibiting the phosphorylation of MKK7 caused by JIK.

A further aspect of the present invention relates to an agent for preventing and/or treating a disorder attributable to c-Jun phosphorylation caused by c-Jun N-terminal kinase 3, having at least one function selected from the group consisting of the following functions:
  i) inhibiting the binding of p21-activated kinase 4 (PAK4) to MAP kinase kinase 7 (MKK7);
  ii) inhibiting the phosphorylation of MKK7 caused by PAK4;
  iii) inhibiting the binding of JNK/SAPK-inhibitory kinase (JIK) to MAP kinase kinase 7 (MKK7); and
  iv) inhibiting the phosphorylation of MKK7 caused by JIK.

A still further aspect of the present invention relates to an agent for preventing and/or treating a neurodegenerative disorder, having at least one function selected from the group consisting of the following functions:
  i) inhibiting the binding of p21-activated kinase 4 (PAK4) to MAP kinase kinase 7 (MKK7);
  ii) inhibiting the phosphorylation of MKK7 caused by PAK4;
  iii) inhibiting the binding of JNK/SAPK-inhibitory kinase (JIK) to MAP kinase kinase 7 (MKK7); and
  iv) inhibiting the phosphorylation of MKK7 caused by JIK.

A further aspect of the present invention relates to a method for preventing and/or treating a disorder attributable to c-Jun phosphorylation caused by c-Jun N-terminal kinase 3, comprising at least one step selected from the group consisting of the following steps:
  i) inhibiting the binding of p21-activated kinase 4 (PAK4) to MAP kinase kinase 7 (MKK7);

ii) inhibiting the phosphorylation of MKK7 caused by PAK4;

iii) inhibiting the binding of JNK/SAPK-inhibitory kinase (JIK) to MAP kinase kinase 7 (MKK7); and iv) inhibiting the phosphorylation of MKK7 caused by JIK.

A still further aspect of the present invention relates to a method for preventing and/or treating a neurodegenerative disorder, comprising at least one step selected from the group consisting of the following steps:

i) inhibiting the binding of p21-activated kinase 4 (PAK4) to MAP kinase kinase 7 (MKK7);

ii) inhibiting the phosphorylation of MKK7 caused by PAK4;

iii) inhibiting the binding of JNK/SAPK-inhibitory kinase (JIK) to MAP kinase kinase 7 (MKK7); and iv) inhibiting the phosphorylation of MKK7 caused by JIK.

A further aspect of the present invention relates to a method for identifying a compound that inhibits the binding of p21-activated kinase 4 (PAK4) to MAP kinase kinase 7 (MKK7), comprising contacting PAK4 and/or MKK7 with a test compound under conditions that allow the binding of PAK4 to MKK7; and determining whether the test compound inhibits the binding of PAK4 to MKK7, by detecting the presence, absence or change of a signal generated by the binding of PAK4 to MKK7.

A still further aspect of the present invention relates to a method for identifying a compound that inhibits the binding of JNK/SAPK-inhibitory kinase (JIK) to MAP kinase kinase 7 (MKK7), comprising contacting JIK and/or MKK7 with a test compound under conditions that allow the binding of JIK to MKK7; and determining whether the test compound inhibits the binding of JIK to MKK7, by detecting the presence, absence or change of a signal generated by the binding of JIK to MKK7.

A further aspect of the present invention relates to a method for identifying a compound that inhibits the phosphorylation of MAP kinase kinase 7 (MKK7) caused by p21-activated kinase 4 (PAK4), comprising contacting PAK4 and/or MKK7 with a test compound; and determining whether the test compound inhibits the phosphorylation of MKK7 caused by PAK4, by introducing a system using a signal and/or a marker capable of detecting the phosphorylation of MKK7 and detecting the presence, absence or change of the signal and/or the marker.

A still further aspect of the present invention relates to a method for identifying a compound that inhibits the phosphorylation of MAP kinase kinase 7 (MKK7) caused by JNK/SAPK-inhibitory kinase (JIK), comprising contacting JIK and/or MKK7 with a test compound; and determining whether the test compound inhibits the phosphorylation of MKK7 caused by JIK, by introducing a system using a signal and/or a marker capable of detecting the phosphorylation of MKK7 and detecting the presence, absence or change of the signal and/or the marker.

A further aspect of the present invention relates to a compound obtained by any one of the aforementioned identification methods.

A still further aspect of the present invention relates to a compound that inhibits the binding of p21-activated kinase 4 (PAK4) to MAP kinase kinase 7 (MKK7).

A further aspect of the present invention relates to a compound that inhibits the binding of JNK/SAPK-inhibitory kinase (JIK) to MAP kinase kinase 7 (MKK7).

A still further aspect of the present invention relates to a compound that inhibits the phosphorylation of MAP kinase kinase 7 (MKK7) caused by p21-activated kinase 4 (PAK4).

A further aspect of the present invention relates to a compound that inhibits the phosphorylation of MAP kinase kinase 7 (MKK7) caused by JNK/SAPK-inhibitory kinase (JIK).

A still further aspect of the present invention relates to an inhibitor of the binding of p21-activated kinase 4 (PAK4) to MAP kinase kinase 7 (MKK7).

A further aspect of the present invention relates to an inhibitor of the binding of JNK/SAPK-inhibitory kinase (JIK) to MAP kinase kinase 7 (MKK7).

A still further aspect of the present invention relates to an inhibitor of the phosphorylation of MAP kinase kinase 7 (MKK7) by p21-activated kinase 4 (PAK4).

A further aspect of the present invention relates to an inhibitor of the phosphorylation of MAP kinase kinase 7 (MKK7) by JNK/SAPK-inhibitory kinase (JIK).

A still further aspect of the present invention relates to a pharmaceutical composition containing an effective amount of at least one member selected from the group consisting of the aforementioned compounds and the aforementioned inhibitors.

A further aspect of the present invention relates to an agent for preventing and/or treating a disorder attributable to c-Jun phosphorylation caused by c-Jun N-terminal kinase 3, containing an effective amount of at least one member selected from the group consisting of the aforementioned compounds and the aforementioned inhibitors.

A still further aspect of the present invention relates to an agent for preventing and/or treating a neurodegenerative disorder, the agent containing an effective amount of at least one member selected from the group consisting of the aforementioned compounds and the aforementioned inhibitors.

A further aspect of the present invention relates to the aforementioned agent for preventing and/or treating a neurodegenerative disorder, wherein the neurodegenerative disorder is a polyglutamine disease, Huntington's disease, spino-cerebellar ataxia, bulbo-spinal muscular atrophy, dentatorubral-pallidoluysian atrophy, Alzheimer's disease, Down syndrome, Parkinson's disease, dementia with Lewy bodies, multisystem atrophy, familial amyotrophic lateral sclerosis, progressive supranuclear palsy, corticobasal degeneration, Pick's disease, familial British dementia, Creutzfeldt-Jakob disease, Gerstmann-Stranssler syndrome, mad cow disease (bovine spongiform encephalopathy) (BSE), or familial dementia associated with neuroserpin inclusion bodies.

A still further aspect of the present invention relates to a method for preventing and/or treating a disorder attributable to c-Jun phosphorylation caused by c-Jun N-terminal kinase 3, comprising using at least one member selected from the group consisting of the aforementioned compounds and the aforementioned inhibitors.

A further aspect of the present invention relates to a method for preventing and/or treating a neurodegenerative disorder, comprising using at least one member selected from the group consisting of the aforementioned compounds and the aforementioned inhibitors.

A still further aspect of the present invention relates to the aforementioned method for preventing and/or treating a neurodegenerative disorder, wherein the neurodegenerative disorder is a polyglutamine disease, Huntington's disease, spino-cerebellar ataxia, bulbo-spinal muscular atrophy, dentatorubral-pallidoluysian atrophy, Alzheimer's disease, Down syndrome, Parkinson's disease, dementia with Lewy bodies, multisystem atrophy, familial amyotrophic lateral sclerosis, progressive supranuclear palsy, corticobasal degeneration, Pick's disease, familial British dementia, Creutzfeldt-Jakob disease, Gerstmann-Stranssler syndrome, mad cow disease (bovine spongiform encephalopathy) (BSE), or familial dementia associated with neuroserpin inclusion bodies.

A further aspect of the present invention relates to a reagent kit containing at least one member selected from the group consisting of p21-activated kinase 4 (PAK4), JNK/SAPK-inhibitory kinase (JIK), a polynucleotide encoding PAK4, a polynucleotide encoding JIK, a vector containing a polynucleotide encoding PAK4 and a vector containing a polynucleotide encoding JIK; and at least one member selected from the group consisting of MAP kinase kinase 7 (MKK7), a polynucleotide encoding MKK7 and a vector containing a polynucleotide encoding MKK7.

A still further aspect of the present invention relates to a reagent kit that is used in the aforementioned identification method, containing at least one member selected from the group consisting of p21-activated kinase 4 (PAK4), JNK/SAPK-inhibitory kinase (JIK), a polynucleotide encoding PAK4, a polynucleotide encoding JIK, a vector containing a polynucleotide encoding PAK4 and a vector containing a polynucleotide encoding JIK; and at least one member selected from the group consisting of MAP kinase kinase 7 (MKK7), a polynucleotide encoding MKK7 and a vector containing a polynucleotide encoding MKK7.

BRIEF DESCRIPTION OF THE DRAWINGS

FIG. 1 illustrates the results of an in-silico prediction of the interaction of MKK7 with PAK4. Local alignment between MKK7 and PAK4 was conducted, and regions with high scores are shown. The upper and lower rows indicate partial sequences present in MKK7 and those in PAK4, respectively.

FIG. 5 illustrates the results of an in-silico prediction of the interaction of MKK7 with JIK. Local alignment between MKK7 and JIK was conducted, and regions with high scores are shown. The upper and lower rows indicate partial sequences present in MKK7 and those in JIK, respectively.

DETAILED DESCRIPTION OF THE INVENTION

Figure 2:
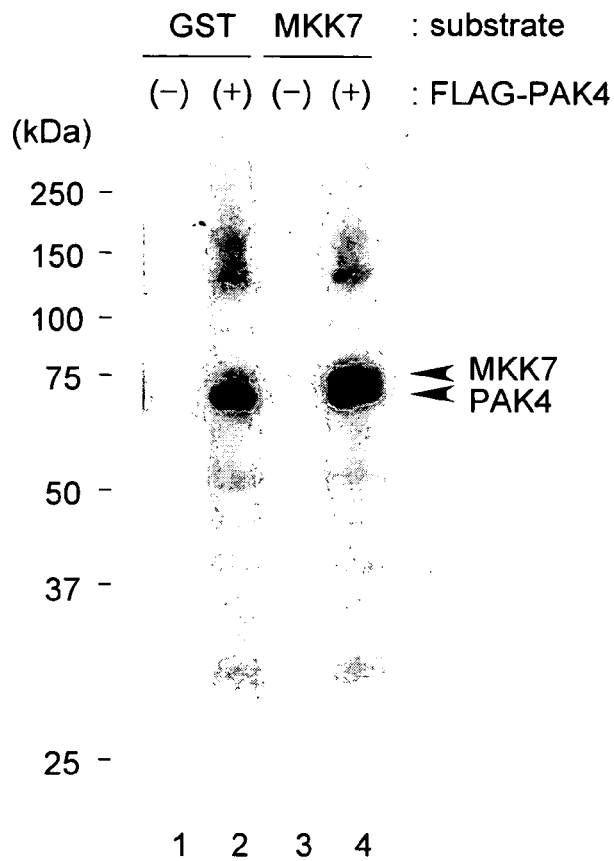
FIG. 2 shows that MKK7 was phosphorylated in-vitro by PAK4. GST-MKK7 was phosphorylated in the presence of FLAG-PAK4 (lane 4), but not phosphorylated in the absence of FLAG-PAK4 (lane 3). On the other hand, GST was not phosphorylated either in the presence (lane 2) or the absence (lane 1) of FLAG-PAK4. -The values shown on the left-hand side of the figure represent molecular weights.

The present invention claims priority from Japanese Patent Application Nos. 2002–190909 and 2002–190910, which are incorporated herein by reference.

Technical and scientific terms used in the present specification have the meanings that are normally understood by those skilled in the art, unless otherwise defined. In the present specification, reference is made to a variety of methods known to those skilled in the art. Publications and other materials disclosing such cited known methods are deemed completely incorporated herein in their entirety by reference. Hereinafter, a mode of embodiment of the present invention may be described in more detail. The following detailed description is illustrative and merely explanatory, and does not limit the present invention in any way.

In the present invention, prediction of proteins that have a function to interact with MKK7 was conducted according to the method set forth in International Patent Publication WO 01/67299; as a result, two proteins were discovered. These proteins are p21-activated kinase 4 (hereinafter abbreviated as PAK4), and JIK, which is one of the STE20-related serine/threonine kinases. Furthermore, it was discovered by experiment, for the first time, that both PAK4 and JIK bind to MKK7 and directly phosphorylate MKK7. In addition, it was revealed that the expression of each of PAK4 and JIK activates c-Jun N-terminal kinase 3 (hereinafter abbreviated as JNK3), which results in the phosphorylation of c-Jun. These findings made it clear that the JNK3 signaling pathway was activated as a result of the direct phosphorylation of MKK7 by each of PAK4 and JIK.

In the present specification, "a protein having a function of interacting with MKK7" refers to a protein that interacts specifically with MKK7, practically, for example, a protein that binds specifically to MKK7 as one of its functions. More practically, "a protein having a function of interacting with MKK7" refers to a protein capable of phosphorylating MKK7 as one of its functions. In the present specification, amino acids may be represented by one letter or three letters.

To date, it is known that PAK4 is activated by cdc42, a low-molecular-weight GTP protein (non-patent document 11). On the other hand, it is reported that the activated cdc42 induces nerve cell death and that the activated cdc42 or PAK4 activates the JNK signaling pathway (non-patent document 7 and 10).

We postulated, from the findings in the present invention in addition to the information shown in those reports, the existence of a signaling pathway that comprises the activation of PAK4 by cdc42, then the binding of activated PAK4 to MKK7 followed by the direct phosphorylation and activation of MKK7, followed by the activation of JNK3, which leads to the phosphorylation of c-Jun, which eventually results in the expression of a certain physiological function. The physiological function can be exemplified by the induction of apoptosis, more practically, the induction of nerve cell death. This finding indicates that it is possible to inhibit the phosphorylation of c-Jun resulting from the activation of JNK3 by inhibiting the binding of PAK4 to MKK7 and/or the phosphorylation of MKK7 caused by PAK4, and further to inhibit nerve cell death. In addition, it can be possible to prevent and/or treat a disorder that is caused by the activation of the JNK3 signaling pathway, including those attributable to the cdc42-mediated activation of the JNK3 signaling pathway.

It is understood that JIK is involved in the activation of JNK caused by ER stress. For example, it is reported that the over-expression of JIK augments the activation of JNK caused by ER stress and that an active-site-deletion mutant of JIK suppresses the activation of JNK caused by ER stress (non-patent document 15).

We postulated, from the findings in the present invention in addition to the information shown in those reports, that the expression of a physiological function caused by ER stress should be mediated by a signaling pathway that comprises the activation of JIK caused by ER stress, then the binding of activated JIK to MKK7, followed by direct phosphorylation and activation of MKK7, which finally results in the activation of JNK3 that leads to the phosphorylation of c-Jun. The physiological function can be exemplified by the induction of apoptosis, more practically, the induction of nerve cell death. This finding indicates that it is possible to inhibit the phosphorylation of c-Jun resulting from the activation of JNK3 by inhibiting the binding of JIK to MKK7 and/or the phosphorylation of MKK7 caused by JIK, and further to inhibit nerve cell death. In addition, it is possible to prevent and/or treat a disorder that is caused by the activation of the JNK3 signaling pathway, such as a disorder attributable to the cdc42-mediated activation of the JNK3 signaling pathway.

A disorder that is caused by the activation of the JNK3 signaling pathway can be exemplified by a disorder attributable to apoptosis, more practically, a neurodegenerative disorder and the like. Examples of a neurodegenerative disorder include polyglutamine diseases (e.g., Huntington's disease, spino-cerebellar ataxia, bulbo-spinal muscular atrophy and dentatorubral-pallidoluysian atrophy), Alzheimer's disease, Down syndrome, Parkinson's disease, dementia with Lewy bodies, multisystem atrophy, familial amyotrophic lateral sclerosis, progressive supranuclear palsy, corticobasal degeneration, Pick's disease, familial British dementia, Creutzfeldt-Jakob disease, Gerstmann-Stranssler syndrome, mad cow disease (bovine spongiform encephalopathy) (BSE), and familial dementia with neuroserpin inclusion bodies (non-patent document 19), but are not limited thereto. In addition to the above examples, nerve cell death caused by ischemia or reperfusion resulting from ER stress can be prevented and/or treated.

The present invention can provide an inhibitor of c-Jun phosphorylation caused by JNK3, a method for inhibiting c-Jun phosphorylation caused by JNK3, and further an agent for preventing and/or treating a disorder attributable to c-Jun phosphorylation caused by JNK3, such as a neurodegenerative disorder, and a method for preventing and/or treating the same, all of which comprises at least one feature selected from the following: i) inhibiting the binding of PAK4 to MKK7; ii) inhibiting the phosphorylation of MKK7 caused by PAK4; iii) inhibiting the binding of JIK to MKK7; and iv) inhibiting the phosphorylation of MKK7 caused by JIK.

The present invention provides, based on the aforementioned findings, a method for identifying a compound that inhibits the binding of PAK4 to MKK7, and/or the phosphorylation of MKK7 caused by PAK4, or a compound that inhibits the binding of JIK to MKK7 and/or the phosphorylation of MKK7 caused by JIK. The identification method can be established using pharmaceutical screening systems that are well-known in the art. PAK4, JIK and MKK7 used for identifying the compound can be contained in cells in which these are expressed by means of genetic engineering techniques, the products of cell-free synthesis systems, chemical synthesis products, or can be those obtained from cells or from any biological samples. These can be subsequently further purified for use. Furthermore, as long as the interaction of PAK4 or JIK with MKK7 and the function of either protein, such as kinase activity, is not disturbed, PAK4, JIK and MKK7 can have a different type of protein or peptide ligated at the N-terminus or the C-terminus thereof, directly or indirectly via a linker peptide and the like, by means of, for example, genetic engineering techniques. Alternatively, PAK4, JIK and MKK7 can be labeled with a chemical modifier. Preferably, the labeling is employed that does not result in inhibiting the basic properties of PAK4, JIK and MKK7. Examples of proteins and peptides to be ligated include enzymes such as glutathione-S-transferase, β-galactosidase, horse radish peroxidase and alkaline phosphatase, tag peptides such as His-tag, Myc-tag, HA-tag, FLAG-tag and Xpress-tag, maltose binding proteins and an Fc fragment of immunoglobulin. Examples of chemical modifiers used for labeling include fluorescent substances (e.g., green fluorescent protein, fluorescein isothiocyanate and phycoerythrin), biotin, and radioactive isotopes. At the time of the labeling, these proteins and peptides can be ligated alone or in combination. Detection of these proteins or peptides themselves used for the labeling, or of the function thereof, makes it possible to determine, for example, the binding of PAK4 or JIK to MKK7. Examples of a compound to be screened include compounds derived from chemical libraries and natural substances, as well as compounds obtained by drug design based on the primary or the three-dimensional structures of PAK4, JIK and MKK7.

A compound that inhibits the binding of PAK4 to MKK7 can be identified, for example, by selecting conditions that allow for the binding of PAK4 to MKK7, contacting PAK4 and MKK7 with a test compound under the conditions, employing an assay system that uses a signal and/or a marker capable of detecting the binding of PAK4 to MKK7, and detecting the presence, the absence, or the change of the signal and/or the marker. For example, when the signal generated by the binding of PAK4 to MKK7 or the marker of the binding exhibits a change such as a disappearance or decrease as a result of the contact of PAK4 and MKK7 with a test compound, it can be determined that the compound inhibits the binding of PAK4 to MKK7. In such an identification method, a test compound can be brought into contact with PAK4 and/or MKK7 in advance of carrying out the binding reaction of PAK4 to MKK7. The term "signal" as used herein refers to a substance that can be detected directly based on its physical properties or chemical properties. The term "marker" refers to a substance that can be detected indirectly by using its physical properties or biological properties as an indicator. For signals, luciferase, green fluorescent protein, radioactive isotopes and the like can be used; for markers, reporter genes such as the chloramphenicol acetyl transferase gene, or detectable tags such as 6×His-tag can be used. However, all substances that are well-known can be used. Methods for detecting these signals and markers are known to those skilled in the art.

Specifically, a compound that inhibits the binding of PAK4 to MKK7 can be identified, for example, by carrying out an evaluation after adding a test compound to a common in-vitro binding assay, which is known to those skilled in the art, comprising fixing either PAK4 or MKK7 on a solid-phase, carrying out a binding reaction using the other one of PAK4 or MKK7, which is labeled with a signal, and measuring quantitatively the signal used for labeling.

Alternatively, a compound that inhibits the phosphorylation of MKK7 caused by PAK4 can be identified by selecting conditions that allow for the phosphorylation of MKK7 by PAK4, contacting PAK4 and MKK7 with a test compound under the conditions, employing an assay system that uses a signal and/or a marker capable of detecting the phosphorylation of MKK7 by PAK4, and detecting the presence, the absence, or the change of the signal and/or the marker. For instance, when the signal resulting from the phosphorylation of MKK7 by PAK4 or the marker of the phosphorylation exhibits change, such as a disappearance or decrease as a result of the contact of PAK4 and MKK7 with a test compound, it can be determined that the compound inhibits the phosphorylation of MKK7 caused by PAK4. In such an identification method, a test compound can be brought into contact with PAK4 and/or MKK7 in advance of carrying out the phosphorylation reaction of MKK7 by PAK4. A protein phosphorylation analysis and quantitative method for measuring phosphorylated protein can be carried out using methods well-known in the art. The protein phosphorylation analysis and quantitative method for measuring phosphorylated protein can be carried out in a simple way, for example, as shown in the examples described below, by bringing PAK4 to react with MKK7 in-vitro in the presence of adenosine triphosphate (ATP) labeled with a radioactive isotope ($^{32}P$), separating the proteins using SDS-PAGE after the reaction, detecting the bands showing the proteins by way of staining, and then, measuring the radioactivity of the band corresponding to the phosphorylated MKK7.

Alternatively, a compound that inhibits the binding of PAK4 to MKK7 and/or the phosphorylation of MKK7 caused by PAK4 can be identified by using cells in which PAK4 and MKK7 have been expressed, bringing the cells into contact with a test compound, employing an assay system using a signal and/or a marker that makes it possible to detect the binding of PAK4 to MKK7 or the phosphorylation of MKK7 by PAK4, and detecting the presence or the absence of the change of the signal and/or the marker.

The identification method using cells as described above can be used in combination with the in-vitro identification methods described above. Compounds that inhibit the binding of PAK4 to MKK7 and /or the phosphorylation of MKK7 caused by PAK4, which are obtained by the in-vitro identification methods as described above, can be subjected to further experimentation with the identification methods using cells as described above, in order to select useful compounds.

When JIK is used in place of PAK4 in the aforementioned identification method, a compound that inhibits the binding of JIK to MKK7 or the phosphorylation of MKK7 caused by JIK can be also identified.

The identification method according to the present invention provides compounds that inhibit the binding of PAK4 to MKK7, compounds that inhibit the binding of JIK to MKK7, compounds that inhibit the phosphorylation of MKK7 caused by PAK4 and compounds that inhibit the phosphorylation of MKK7 caused by JIK. These compounds are also included in the scope of the present invention. These compounds are available as inhibitors of the binding of PAK4 to MKK7, inhibitors of the phosphorylation of MKK7 by PAK4, inhibitors of the binding of JIK to MKK7 and inhibitors of the phosphorylation of MKK7 by JIK. Such compounds can be exemplified by peptides or oligopeptides, comprising the amino acid sequences of the interaction sites such as, for example, the binding sites of the two proteins. Such peptides or oligopeptides can be identified by designing them from the amino acid sequence of PAK4 or MKK7, synthesizing them by peptide synthesis methods well-known in the art, and examining, in the identification method described above, whether they can inhibit the binding of PAK4 to MKK7, the phosphorylation of MKK7 caused by PAK4, the binding of JIK to MKK7 or the phosphorylation of MKK7 caused by JIK. Examples of the aforementioned compounds also include antibodies capable of inhibiting the binding of PAK4 to MKK7 or the binding of JIK to MKK7. Such antibodies can be obtained by preparing the antibodies against PAK4, JIK or MKK7 and selecting the one capable of inhibiting the binding of PAK4 to MKK7 or the binding of JIK to MKK7 among the antibodies obtained. Antibodies can be produced, for example, using each protein itself such as PAK4, JIK and MKK7, or the peptides or the oligopeptides (comprising the amino acid sequences of the interaction sites of PAK4 with MKK7 or of JIK with MKK7) as an antigen, by using antibody preparation methods well-known in the art.

The thus-selected compounds, binding inhibitors and phosphorylation inhibitors can be used as effective ingredients in a medicament based on inhibiting the binding of PAK4 to MKK7, the binding of JIK to MKK7, the phosphorylation of MKK7 by PAK4 or the phosphorylation of MKK7 by JIK, by way of further selection with consideration given to the balance between the biological effectiveness and toxicity thereof. Both PAK4 and JIK directly phosphorylate and activate MKK7 after binding to MKK7, which results in the activation of JNK3, followed by the phosphorylation of c-Jun. Therefore, the aforementioned compounds, binding inhibitors and phosphorylation inhibitors can be used as an effective ingredient in a medicament for a disorder attributable to c-Jun phosphorylation by JNK3, such as a disorder attributable to apoptosis, practically, a neurodegenerative disorder.

The medicament according to the present invention can be a medicament containing an effective dose of at least one member selected from the group consisting of the aforementioned compounds, binding inhibitors and phosphorylation inhibitors, but it is preferably a pharmaceutical composition formulated in combination with suitable pharmaceutical acceptable carriers or vehicles. Examples of a carrier include physiological saline, buffered physiological saline, dextrose, water, glycerol, ethanol, and a mixture thereof; however, they are not limited thereto.

Suitable dosage ranges can be determined according to the following: effectiveness of the aforementioned compounds, binding inhibitors and phosphorylation inhibitors; the route of administration; the type of the disorder; the characteristics of the subject (e.g., body weight, age, symptomatic conditions and whether being taking other medicaments); and the judgment of the doctor in charge. More specifically, a suitable dosage may fall within the range of, e.g., 0.1 µg to 10 µg per 1 kg of the body weight of the subject. However, the dosage may be altered using common conventional experiments for optimization of a dosage that are well known in the art. The aforementioned dosage can be divided for administration once to four times a day. Alternatively, periodic administration once every few days or few weeks can be employed.

In terms of a formulation, the formulation can be selected according to an administration route, and such formulations are well-known to those skilled in the art. At the time of formulation, the compositions can be used alone or in combination with other compounds or medicaments required for treatment. For example, an effective ingredient, such as a c-Jun phosphorylation inhibitor or an agent for preventing and/or treating for a nerve degenerative disorder can be formulated together.

In terms of the mode of administration, it may be either systemic administration or local administration. A mode of administration that is appropriate for a particular disorder, symptomatic conditions, or other factors should be selected. One preferred mode of systemic administration is injection, e.g., an intravenous injection or intra-arterial injection. Other injection routes, such as subcutaneous, intramuscular, or intraperitoneal injection, may also be used. Another mode of administration may be oral administration, so long as an enteric formulation or a capsule formulation can be suitably formulated. In addition, transmucosal administration or percutaneous administration, which comprises using a penetrant such as bile salt, fusidic acid, or other surfactants, may also be used. In a local administration, forms such as ointments, pastes, or gels, may be used.

Preparation of a pharmaceutical may be carried out by well-known formulating procedures, where a suitable carrier for formulation can be used in accordance with the mode of administration or the physical properties of the effective ingredient therein. Specifically, formulations such as powdered drugs, pills, tablets, capsules, aqueous solutions, ethanol solutions, liposomal formulations, fat emulsions, clathrates (such as those of cyclodextrin), and the like can be used.

Powdered drugs, pills, capsules, or tablets can be prepared using, for example, an excipient such as lactose, glucose, sucrose, or mannitol; a disintegrant such as starch or sodium arginate; a lubricant such as magnesium stearate or talc; a binder such as polyvinylalcohol, hydroxypropyl cellulose, or gelatin; a surfactant such as fatty acid ester; and a plasticizer such as glycerin, or the like. For preparation of a tablet or capsule, a solid pharmaceutical acceptable carrier is used.

A suspension can be prepared using water, saccharides such as sucrose, sorbitol, or fructose, glycols such as PEG, and oils.

Injectable solutions can be prepared using a carrier comprising a salt solution, a glucose solution, or a mixture of a salt solution and a glucose solution.

Inclusion into a liposome formulation may be conducted in the following manner: by dissolving the substance of interest in a solvent (e.g., ethanol) to make a solution, adding a solution of phospholipids dissolved in an organic solvent (e.g., chloroform), removing the solvent by evaporation and adding a phosphate buffer thereto, agitating the solution and then subjecting it to sonication followed by centrifugation to obtain supernatant, and finally, filtrating the supernatant to recover liposomes.

A fat emulsion can be prepared in the following manner: by mixing the substance of interest, an oil ingredient (vegetable oil such as soybean oil, sesame oil, olive oil, or MCT), an emulsifier (such as a phospholipid), and the like; heating the mixture to make a solution; adding water of a required quantity; and then emulsifying or homogenizing by use of an emulsifier (a homogenizer, e.g., a high pressure jet type, an ultrasonic type, or the like). The fat emulsion may be also lyophilized. For conducting lipid-emulsification, an auxiliary emulsifier may be added, and examples thereof include glycerin or saccharides (e.g., glucose, sorbitol, fructose, etc.).

Inclusion into a cyclodextrin formulation may be carried out in the following manner: by dissolving the substance of interest in a solvent (e.g., ethanol); adding a solution of cyclodextrin dissolved in water under heating thereto; chilling the solution and filtering the precipitates; and drying under sterilization. At this time, the cyclodextrin to be used may be appropriately selected from among those having different void sizes ($\alpha$, $\beta$, or $\gamma$ type) in accordance with the bulkiness of the substance of interest.

The present invention provides a reagent kit that includes at least one member selected from the group consisting of PAK4, JIK, a polynucleotide encoding PAK4, a polynucleotide encoding JIK, a vector containing the polynucleotide encoding PAK4 and a vector containing the polynucleotide encoding JIK, along with at least one member selected from the group consisting of MKK7, a polynucleotide encoding MKK7 and a vector containing the polynucleotide encoding MKK7. JIK, PAK4 and MKK7 can be contained in cells in which these are expressed by means of genetic engineering techniques, the products of cell-free synthesis systems, chemical synthesis products, or can be obtained from cells or from any biological samples. These can be subsequently further purified for use. Furthermore, as long as the binding of JIK or PAK4 to MKK7 and the function of these proteins, such as kinase activity, is not disturbed, JIK, PAK4 and MKK7 can have a different type of protein or peptide ligated at the N-terminus or the C-terminus thereof, directly or indirectly via a linker peptide and the like, by means of, for example, genetic engineering techniques. Alternatively, PAK4, JIK and MKK7 can be labeled with a chemical modifier. Preferably, the labeling is employed that does not result in inhibiting the basic properties of PAK4, JIK and MKK7. Examples of proteins and peptides to be ligated include enzymes such as glutathione-S-transferase, $\beta$-galactosidase, horse radish peroxidase and alkaline phosphatase, tag peptides such as His-tag, Myc-tag, HA-tag, FLAG-tag and Xpress-tag, maltose binding proteins and an Fc fragment of immunoglobulin. Examples of chemical modifiers used for the labeling include fluorescent substances (e.g., green fluorescent protein, fluorescein isothiocyanate and phycoerythrin), biotin, and radioactive isotopes. At the time of the labeling, these proteins and peptides can be ligated alone or in combination. A polynucleotide encoding any one of PAK4, JIK and MKK7 can be prepared from human cDNA library using genetic engineering techniques that are well known in the art. A vector containing the polynucleotide encoding any one of PAK4, JIK and MKK7 can be obtained by introducing the polynucleotide into a suitable expression vector DNA, such as a vector derived from a bacterial plasmid, using genetic engineering techniques that are well known in the art. The reagent kit may contain required substances, such as a signal and/or marker for detecting the binding of PAK4 or JIK to MKK7, or for detecting the phosphorylation of MKK7 by PAK4 or JIK, a buffer, and a salt. Further, they may contain a stabilizer and/or antiseptic agent. In terms of the preparation thereof, it is sufficient to use a well-known means to prepare each substance.

EXAMPLES

Hereinafter, the present invention may be explained more particularly with an example; however, the present invention is not limited to the following examples.

Example 1

In-Silico Search for Proteins Having a Function of Interacting with MKK7

The prediction of proteins having a function of interacting with MKK7 was conducted according to the method set forth in the International Patent Publication No: WO 01/67299. First, the amino acid sequence of MKK7 was decomposed into oligopeptides having a pre-determined length in order to search in a database for proteins having the amino acid sequence of each of the oligopeptides, or having homologous amino acid sequences to these amino acid sequences. Next, local alignment was conducted between the proteins obtained and MKK7 to identify proteins having a high local alignment score and that might be capable of interacting with MKK7.

As a result of the analysis, it was found that the oligopeptides DIWSLGI (SEQ ID NO: 3) and PPARAR (SEQ ID NO: 4), which have homology to the oligopeptides DVWSLGI (SEQ ID NO: 1) and PPARPR (SEQ ID NO: 2) that consist of seven or six amino acid residues derived from MKK7, are present in the amino acid sequence of the PAK4. FIG. 1 shows the results of local alignment between MKK7 and PAK4. From these results, PAK4 was predicted to be a protein having a function of interacting with MKK7.

Example 2

Analysis of the Phosphorylation of MKK7 by PAK4

In order to experimentally determine the interaction of PAK4 with MKK7, an in-vitro phosphorylation experiment was conducted using the immune complex phosphorylation method.

<Materials>

A PAK4 expression plasmid was constructed as follows. First, human PAK4 cDNA was obtained from human-brain-derived poly(A)$^+$RNA (Clontech) by a reverse transcription polymerase chain reaction (RT-PCR), and then inserted into pcDNA3.1(+) (Invitrogen) which is an expression vector for an animal cell expression system. At the time of insertion of the cDNA into the vector, a FLAG-tag coding sequence or HA-tag coding sequence was inserted at the 5' side, and thereby there were constructed respectively an expression plasmid for an animal cell expression system comprising PAK4 ligated with FLAG-tag at its N-terminus (pcDNA-FLAG-PAK4) and comprising PAK4 ligated with HA-tag at its N-terminus (pcDNA-HA-PAK4).

Buffers comprising the following compositions were used in the experiments.

Cell lysis buffer: 20 mM Tris-HCl, pH 7.4, 150 mM NaCl, 1 mM ethylene diamine tetraacetic acid (EDTA), 1 mM ethylene glycol bis-tetraacetic acid (EGTA), 1% Triton X-100, 2.5 mM Na-pyrophosphate, 1 mM β-glycerophosphate, 1 mM $Na_3VO_4$, protease inhibitor cocktail (Cell Signaling Technology).

Kinase buffer: 25 mM Tris-HCl, pH 7.5, 5 mM β-glycerophosphate, 2 mM dithiothreitol, 0.1 mM $Na_3VO_4$, 10 mM $MgCl_2$ (Cell Signaling Technology).

SDS sample buffer: 4% SDS, 125 mM Tris-HCl, pH 6.8, 20% glycerol, 0.01% bromo phenol blue (BPB), 10% β-mercaptoethanol.

<Method>

After HEK293 cells ($5 \times 10^5$ cells in a dish with 60 mm diameter) were cultured overnight at 37° C. in 5% $CO_2$, the cells were transfected with 5 μg pcDNA-FLAG-PAK4 by using 15 μl FuGENE6 Transfection Reagent (Roche). The transfection was similarly conducted using pcDNA3.1(+) as a negative control. After culturing for two days, cells were rinsed with ice-cold phosphate-buffered physiological saline (−) (PBS (−)), collected and suspended in the 500 μl cell lysis buffer, and left standing on ice for 10 minutes. Then, the cells were subjected to centrifugation at 14,000 rpm for 10 minutes at 4° C. to collect the supernatant for use as a cell lysate. Next, 500 μl cell lysate was mixed with 20 μl agarose-conjugated normal mouse IgG (Sigma) by inversion for 30 minutes at 4° C., followed by centrifugation to collect the supernatant. The collected supernatant was mixed with 20 μl anti-FLAG M2 affinity gel (Sigma) by inversion for two hours at 4° C. Then, the beads were collected by centrifugation and washed twice with 500 μl cell lysis buffer and twice with 500 μl kinase buffer. Next, the beads were mixed with 25 μl kinase buffer containing 1 μg substrate, 10 μM ATP and 5μCi [γ-$^{32}$P]ATP (3,000 Ci/mmol, PerkinElmer) and a phosphorylation reaction was allowed to proceed for 30 minutes at 30° C. After the reaction, 25 μl 2×SDS sample buffer was added. After boiling for five minutes, the supernatant was separated by SDS-PAGE and phosphorylated proteins were detected by autoradiography using BAS2000 (Fuji film). As a substrate, unactive GST-MKK7 (Upstate) was used, while GST was used for a negative control.

<Results>

The phosphorylation of GST-MKK7 by PAK4 was observed as shown in FIG. 2. Since such phosphorylation was not observed in the absence of PAK4, it was revealed that the phosphorylation of GST-MKK7 was not self-phosphorylation, but was caused by PAK4. The phosphorylation was not observed when GST was used as a substrate for a negative control.

Example 3

Analysis of the Binding of PAK4 to MKK7

In order to experimentally determine the binding of PAK4 to MKK7, a binding test was conducted using the intracellular-co-expression/immuno-co-precipitation method.

<Materials>

For the PAK4 expression plasmid, the plasmid constructed in example 2 was used.

An MKK7 expression plasmid was constructed as follows. First, human MKK7 cDNA was obtained from human skeletal muscle-derived poly(A)$^+$RNA (Clontech) by RT-PCR and then inserted into pcDNA3.1(+) (Invitrogen) which is an expression vector for an animal cell expression system. At the time of insertion of the cDNA into the vector, an HA-tag coding sequence was inserted at the 5' side, and thereby an expression plasmid for an animal cell expression system of MKK7 ligated with HA-tag at its N-terminus (pcDNA-HA-MKK7) was constructed.

The buffers used in the experiments were the same in composition as those described in Example 2.

<Method>

After HEK293T cells ($4 \times 10^5$ cells in a dish with 60 mm diameter) were cultured overnight at 37° C. in 5% $CO_2$, the cells were transfected with 2 µg pcDNA-FLAG-PAK4 along with 2 µg pcDNA-HA-MKK7 by using FuGENE6 Transfection Reagent (Roche). The transfection was similarly conducted using pcDNA3.1(+) as a negative control. After culturing for two days, cells were rinsed with ice-cold PBS (-), collected and suspended in the 500 µl cell lysis buffer, and left standing on ice for 10 minutes. Then, the cells were subjected to centrifugation at 14,000 rpm for 10 minutes at 4° C. to collect the supernatant for use as a cell lysate. Next, 500 µl cell lysate was mixed with 20µl agarose-conjugated normal mouse IgG (Sigma) by inversion for 30 minutes at 4° C., followed by centrifugation to collect the supernatant. The collected supernatant was mixed with 20 µl anti-FLAG M2 affinity gel (Sigma) by inversion overnight at 4° C. Then, the beads were collected by centrifugation, washed three times with 500 µl cell lysis buffer and once with 500 µl Tris-buffered physiological saline (TBS: 25 mM Tris-HCl, pH 7.5, 150 mM NaCl), and then mixed with 20 µl 2×SDS sample buffer. After boiling for five minutes, the supernatant was separated by 5–20% SDS-PAGE. Then, binding proteins were detected by western blotting using an anti-HA antibody (Y-11, SantaCruz). An ECL western blotting detection kit (Amersham pharmacia biotech) was used for the detection.

<Results>

Figure 3:
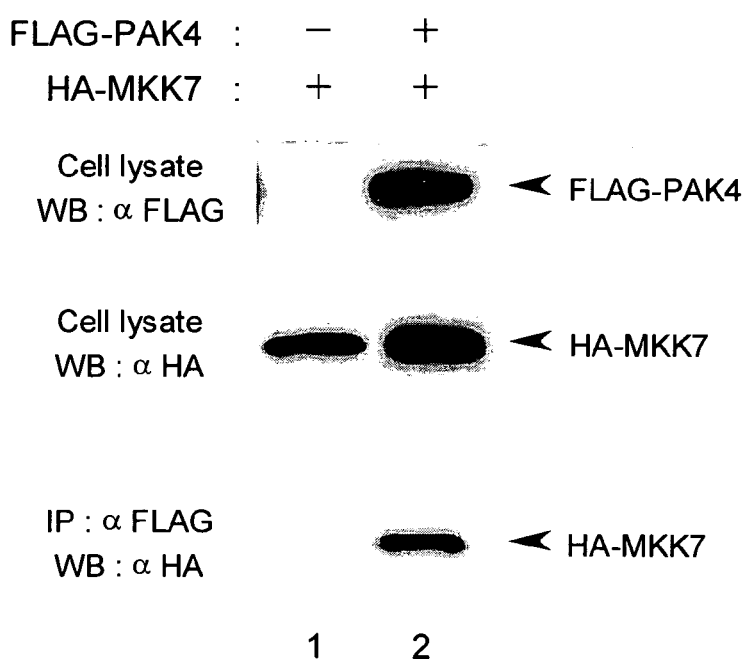
FIG. 3 shows that the binding of PAK4 to MKK7 was observed in a cell. The bottom panel of the figure shows the result of an immunoprecipitation test (IP), indicating that an immunoprecipitate containing HA-MKK7 and FLAG-PAK4 was detected in a cell lysate prepared from cells co-expressing HA-MKK7 and FLAG-PAK4 (lane 2), though such an immunoprecipitate was not detected in a cell lysate prepared from cells expressing only HA-MKK7 (lane 1). The top and middle panels, respectively, show the results of verification of the expression of FLAG-PAK4 and HA-MKK7 in each cell lysate. Detection of the immunoprecipitate and verification of the expression were both carried out by western blotting (WB).

As a result of the immuno-precipitation of FLAG-PAK4 using an anti-FLAG antibody, HA-MKK7 was co-precipitated therewith when using the cells co-expressing FLAG-PAK4 and HA-MKK7, as shown in FIG. 3. On the other hand, HA-MKK7 was not co-precipitated when using the cells not expressing FLAG-PAK4, which revealed that such co-precipitation resulted from the binding of FLAG-PAK4 to HA-MKK7 rather than nonspecific binding to the agarose beads. These findings revealed that PAK4 binds to MKK7 in a cell.

Example 4

Activation of the JNK3 Signaling Pathway by PAK4

In order to experimentally determine the activation of the JNK3 signaling pathway by PAK4, an in-vitro JNK3 phosphorylation experiment was conducted using the immune complex phosphorylation method.

<Materials>

For a PAK4 expression plasmid, the plasmid constructed in example 2 was used.

A JNK3 expression plasmid was constructed as follows. First, human JNK3 cDNA was obtained from a human hippocampal cDNA library by RT-PCR, and then inserted into pcDNA3.1(+) (Invitrogen) which is an expression vector for an animal cell expression system. At the time of the insertion of the cDNA into the vector, a FLAG-tag coding sequence was inserted at the 5' side, and thereby an expression plasmid for an animal cell expression system of JNK3 ligated with FLAG-tag at its N-terminus (pcDNA-FLAG-JNK3) was constructed.

Meanwhile, c-Jun (1-79) (a region of c-Jun consisting of its N-terminal 79 amino acids that includes the JNK phosphorylation site) was expressed as a fusion protein ligated with GST (glutathione S-transferase) at its N-terminus (hereinafter, GST-c-Jun (1-79)) in *Escherichia coli*, and then purified with glutathione sepharose 4B (Amersham Pharmacia biotech) for use.

The solutions used in the experiment were the same in composition as those described in Example 2.

<Method>

After HEK293 cells ($6 \times 10^5$ cells in a dish with 60 mm diameter) were cultured overnight at 37° C. in 5% $CO_2$, the cells were transfected with pcDNA-FLAG-JNK3 (2 µg) and pcDNA-HA-PAK4 (0, 0.1, 0.5 or 2 µg) by using 12 µl FuGENE6 Transfection Reagent (Roche). The total amount of DNA was adjusted to 4 µg each using pcDNA 3.1(+). After culturing for two days, the cells were rinsed with ice-cold PBS (-), collected and suspended in the 500 µl cell lysis buffer, and left standing on ice for 10 minutes. Then, the cells were subjected to centrifugation at 14,000 rpm for 10 minutes at 4° C. to collect the supernatant for use as a cell lysate. Next, 500 µl cell lysate was mixed with 20 µl agarose-conjugated normal mouse IgG (Sigma) by inversion for 30 minutes at 4° C., followed by centrifugation to collect the supernatant. The collected supernatant was mixed with 20 µl anti-FLAG M2 affinity gel (Sigma) by inversion for two-hours at 4° C. Then, the beads were collected by centrifugation and washed twice with 500 µl cell lysis buffer and twice with 500 µl kinase buffer. Next, the beads were mixed with 25 µl kinase buffer containing 2 µg GST-c-Jun (1-79) as a substrate, 10 µM ATP and 5µCi [γ-$^{32}$P]ATP (3,000 Ci/mmol, PerkinElmer) and the phosphorylation reaction was allowed to proceed for 30 minutes at 30° C. After the reaction, 25 µl 2×SDS sample buffer was added. After boiling for five minutes at 100° C., the supernatant was separated by SDS-PAGE and the phosphorylated GST-c-Jun (1-79) was detected by autoradiography using BAS2000 (Fuji film). The expression of each protein was detected by western blotting using anti-FLAG M2 monoclonal antibody (Sigma) or anti-HA antibody (Y-11, SantaCruz).

<Results>

Figure 4:
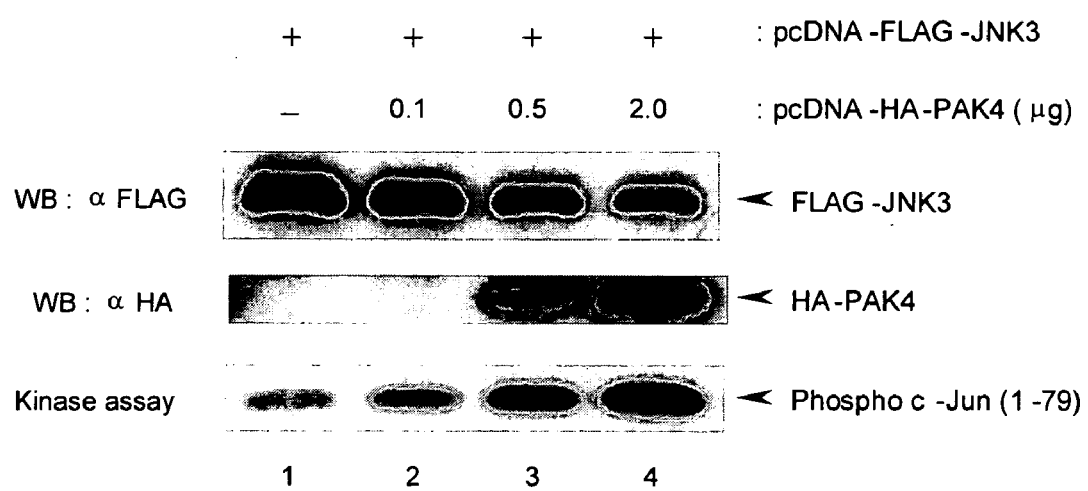
FIG. 4 shows that the temporary expression of PAK4 increased c-Jun phosphorylation by JNK3 dependently on the amount of expressed PAK4. The bottom panel in the figure shows the result of a kinase assay, indicating that GST-c-Jun(1-79) was phosphorylated when using a cell lysate prepared from cells co-expressing HA-PAK4 and FLAG-JNK3 (lanes 2–4), but not phosphorylated when using a cell lysate prepared from cells expressing only FLAG-JNK3 (lanes 1). Lanes 2, 3 and 4 show the results when transfecting with an HA-PAK4 expression vector (pcDNA-HA-PAK4) in amounts of 0.1 μg, 0.5 μg and 2.0 μg, respectively. The top and middle panels show respectively the results of verification of the expression of FLAG-JNK3 and HA-PAK4. The verification of expression was carried out by western blotting (WB).

Phosphorylated c-Jun increased depending on the amount of expressed HA-PAK4, in the kinase assay using a lysate of cells co-expressing HA-PAK4 and FLAG-JNK3, as shown in FIG. 4. Specifically, it was revealed that the expression of HA-PAK4 increases the c-Jun phosphorylation activity of JNK3. Since the amount of expressed FLAG-JNK3 did not show a large variation, the increase in JNK3 activity can be considered to result from the expression of HA-PAK4.

The results obtained in the examples 2, 3 and 4 revealed that PAK4 binds to MKK7 and directly phosphorylates MKK7, which results in the activation of JNK3 followed by the phosphorylation of c-Jun, that is to say, the activation of JNK3 signaling pathway.

Example 5

In-silico Search for Proteins Having a Function of Interacting with MKK7

The prediction of proteins having a function of interacting with MKK7 was conducted in the same way as in Example 1. As a result, it was found that the oligopeptides WSLGIT (SEQ ID NO: 7) and LENKLK (SEQ ID NO: 8), which have homology to the oligopeptides WSLGIS (SEQ ID NO: 5) and LEAKLK (SEQ ID NO: 6) that consist of six amino acid residues derived from MKK7, are present in the amino acid sequence of the JIK. FIG. 5 shows the results of local alignment between MKK7 and JIK. From these results, JIK was predicted to be a protein having a function of interacting with MKK7.

Example 6

Analysis of the Phosphorylation of MKK7 by JIK

In order to experimentally determine the phosphorylation of MKK7 by JIK, an in-vitro phosphorylation experiment was conducted using the immune complex phosphorylation method.

<Materials>

A JIK expression plasmid was constructed as follows. First, human JIK cDNA was obtained from human kidney-derived poly(A)⁺RNA (Clontech) by RT-PCR, and then inserted into pcDNA3.1(+) (Invitrogen) which is an expression vector for an animal cell expression system. At the time of insertion of the cDNA into the vector, an HA-tag coding sequence was inserted at the 5' side, and thereby an expression plasmid for an animal cell expression system of JIK ligated with HA-tag at its N-terminus (pcDNA-HA-JIK) was constructed. The coding amino acid sequence of cloned JIK cDNA is the same as that of the accession number XP_045006 (registered gene name: JIK) disclosed in the NCBI (National Center for Biotechnology Information) protein database.

The buffers used in the experiment were the same in composition as those described in Example 2.

<Method>

After HEK293T cells (4×10⁵ cells in a dish with 60 mm diameter) were cultured overnight at 37° C. in 5% $CO_2$, the cells were transfected with 5 μg pcDNA-HA-JIK by using 15 μl FuGENE6 Transfection Reagent (Roche). The transfection was similarly conducted using pcDNA3.1(+) as a negative control. After culturing for two days, cells were rinsed with ice-cold PBS (−), collected and suspended in the 500 μl cell lysis buffer, and left standing on ice for 10 minutes. Then, the cells were subjected to centrifugation at 14,000 rpm for 10 minutes at 4° C. to collect the supernatant for use as a cell lysate. Next, 500 μl cell lysate was mixed with 20 μl agarose-conjugated normal mouse IgG (Sigma) by inversion for 30 minutes at 4° C., followed by centrifugation to collect the supernatant. The collected supernatant was mixed with 20 μl anti-HA affinity matrix (Roche) by inversion for two hours at 4° C. Then, the beads were collected by centrifugation and washed twice with 500 μl cell lysis buffer and twice with 500 μl kinase buffer. Next, the beads were mixed with 25 μl kinase buffer containing 1 μg substrate, 10 μM ATP and 5μCi [γ-³²P]ATP (3,000 Ci/mmol, PerkinElmer) and the phosphorylation reaction was allowed to proceed for 30 minutes at 30° C. After the reaction, 25 μl 2×SDS sample buffer was added. After boiling for five minutes, the supernatant was separated by SDS-PAGE and phosphorylated proteins were detected by autoradiography using BAS2000 (Fuji film). As a substrate, inactive GST-MKK7 (Upstate) was used, while GST was used for a negative control.

<Results>

Figure 6:
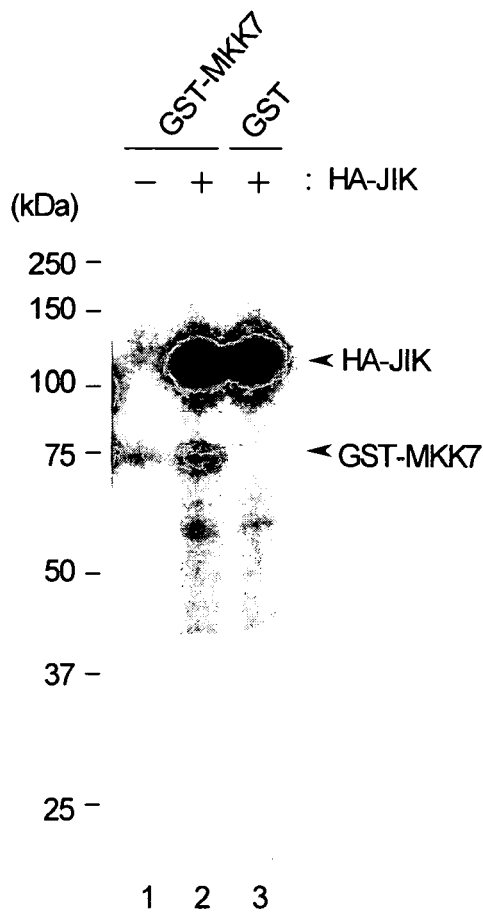
FIG. 6 shows that MKK7 was phosphorylated in-vitro by JIK. GST-MKK7 was phosphorylated in the presence of HA-JIK (lane 2), but not phosphorylated in the absence of HA-JIK (lane 1). On the other hand, GST was not phosphorylated in the presence (lane 3) of HA-JIK. The values shown on the left-hand side of the figure represent molecular weights.

The phosphorylation of GST-MKK7 by JIK was observed as shown in FIG. 6. Since such phosphorylation was not observed in the absence of JIK, it was revealed that the phosphorylation of GST-MKK7 was not self-phosphorylation, but was caused by JIK. The phosphorylation was not observed when GST was used as a substrate for a negative control.

Example 7

Analysis of the Binding of JIK to MKK7

In order to experimentally determine the binding of JIK to MKK7, a binding test was conducted using the intracellular-co-expression/immuno-co-precipitation method.

<Materials>

For a JIK expression plasmid, the plasmid constructed in example 6 was used.

An MKK7 expression plasmid was constructed as follows. First, human MKK7 cDNA was obtained from human skeletal muscle-derived poly(A)⁺RNA (Clontech) by RT-PCR, and then inserted into pcDNA3.1(+) (Invitrogen) which is an expression vector for an animal cell expression system. At the time of insertion of the cDNA into the vector, FLAG-tag coding sequence was inserted at the 5' side, and thereby an expression plasmid for an animal cell expression system of MKK7 ligated with FLAG-tag at its N-terminus (pcDNA-FLAG-MKK7) was constructed.

The buffers used in this test were the same in composition as those described in Example 2.

<Method>

After HEK293T cells (4×10⁵ cells in a dish with 60 mm diameter) were cultured overnight at 37° C. in 5% $CO_2$, the cells were transfected with 2 μg pcDNA-HA-JIK along with 2 μg pcDNA-FLAG-MKK7 by using FuGENE6 Transfection Reagent (Roche). The transfection was similarly conducted using pcDNA3.1(+) as a negative control. After culturing for two days, cells were rinsed with ice-cold PBS (−), collected and suspended in the 500 μl cell lysis buffer, and left standing on ice for 10 minutes. Then, the cells were subjected to centrifugation at 14,000 rpm for 10 minutes at 4° C. to collect the supernatant for use as a cell lysate. Next, 500 μl cell lysate was mixed with 20 μl agarose-conjugated normal mouse IgG (Sigma) by inversion for 30 minutes at 4° C., followed by centrifugation to collect the supernatant. The collected supernatant was mixed with 20 μl anti-HA affinity matrix (Roche) by inversion overnight at 4° C. Then, the beads were collected by centrifugation, washed three times with 500 μl cell lysis buffer and once with 500 μl TBS (25 mM Tris-HCl, pH 7.5, 150 mM NaCl), and then mixed with 20 μl 2×SDS sample buffer. After boiling for five minutes, the supernatant was separated by 5–20% SDS-PAGE. Then, binding proteins were detected by western blotting using an anti-FLAG M2 antibody (Sigma). An ECL western blotting detection kit was used for the detection.

<Results>

Figure 7:
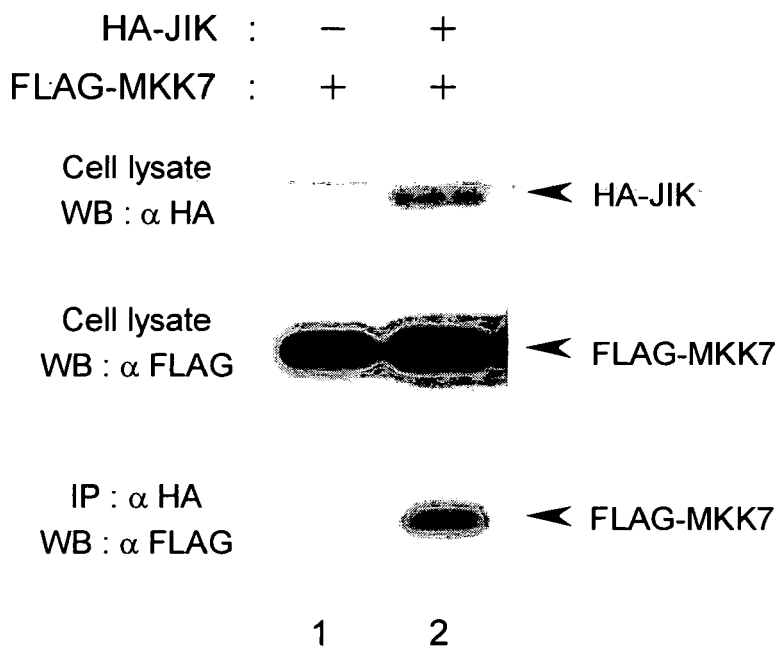
FIG. 7 shows that the binding of JIK to MKK7 was observed in a cell. The bottom panel of the figure shows the result of immunoprecipitation test (IP), indicating that an immunoprecipitate containing FLAG-MKK7 and HA-JIK was detected in a cell lysate prepared from cells co-expressing FLAG-MKK7 and HA-JIK (lane 2), though such an immunoprecipitate was not detected in a cell lysate prepared from cells expressing only FLAG-MKK7 (lane 1). The top and middle panels, respectively, show the results of the verification of expression of HA-JIK and FLAG-MKK7 in each cell lysate. Detection of the immunoprecipitate and verification of the expression were both carried out by western blotting (WB).

As a result of the immuno-precipitation of HA-JIK using the anti-HA antibody, FLAG-MKK7 was co-precipitated therewith when using the cells co-expressing HA-JIK and FLAG-MKK7, as shown in FIG. 7. On the other hand, FLAG-MKK7 was not co-precipitated when using the cells not expressing HA-JIK, which revealed that such co-precipitation resulted from the binding of HA-JIK to FLAG-MKK7 rather than nonspecific binding to the agarose beads. These findings revealed that JIK binds to MKK7 in a cell.

Example 8

Activation of the JNK3 Signaling Pathway by JIK

In order to experimentally determine the activation of the JNK3 signaling pathway by JIK, an in-vitro JNK3 phosphorylation experiment was conducted using the immune complex phosphorylation method.

<Materials>

For a JNK3 expression plasmid, the plasmid constructed in example 4 was used.

For a JIK expression plasmid, the plasmid constructed in example 6 was used.

GST-c-Jun (1-79) was prepared in the same manner as in example 4.

The buffers used in this test were the same in composition as those described in Example 2.

<Method>

After HEK293T cells ($4 \times 10^5$ cells in a dish with 60 mm diameter) were cultured overnight at 37° C. in 5% $CO_2$, the cells were transfected with 2 μg pcDNA-HA-JIK and 2 μg pcDNA-FLAG-JNK3 by using FuGENE6 Transfection Reagent (Roche). The transfection was similarly conducted using pcDNA3.1(+) as a negative control. After culturing for two days, cells were rinsed with ice-cold PBS (–), collected and suspended in the 500 μl cell lysis buffer, and left standing on ice for 10 minutes.

Then, the cells were subjected to centrifugation at 14,000 rpm for 10 minutes at 4° C. to collect the supernatant for use as a cell lysate. Next, 500 μl cell lysate was mixed with 20 μl agarose-conjugated normal mouse IgG (Sigma) by inversion for 30 minutes at 4° C., followed by centrifugation to collect the supernatant. The collected supernatant was mixed with 20 μl anti-FLAG M2 affinity gel (Sigma) by inversion for two hours at 4° C. Then, the beads were collected by centrifugation and washed twice with 500 μl cell lysis buffer and twice with 500 μl kinase buffer. Next, the beads were mixed with 25 μl kinase buffer containing 2 μg GST-c-Jun (1-79) as a substrate, 10 μM ATP and 5μCi [γ-$^{32}$P]ATP (3,000Ci/mmol, PerkinElmer) and the phosphorylation reaction was allowed to proceed for 30 minutes at 30° C. After the reaction, 25 μl 2×SDS sample buffer was added. After boiling for five minutes at 100° C., the supernatant was separated by SDS-PAGE and the phosphorylated GST-c-Jun (1-79) was detected by autoradiography using BAS2000 (Fuji film).

<Results>

Figure 8:
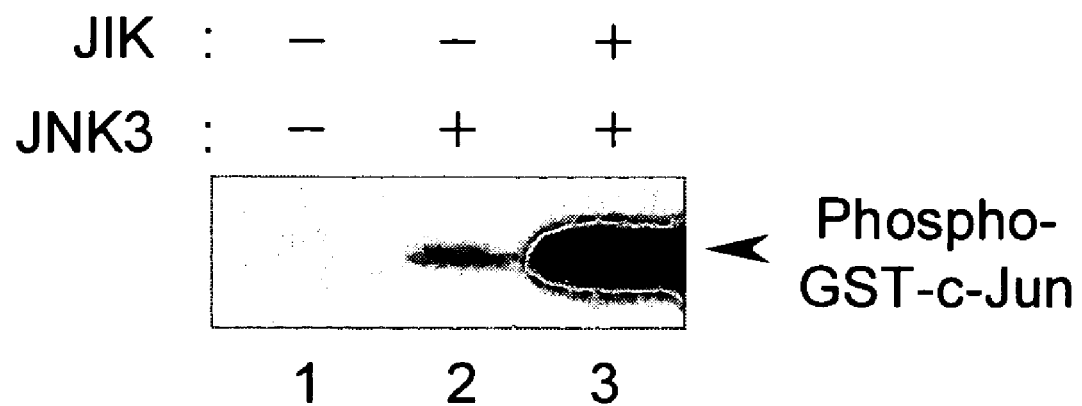
FIG. 8 shows that the temporary expression of JIK increased c-Jun phosphorylation caused by JNK3. GST-c-Jun(1-79) was phosphorylated when using a cell lysate prepared from cells co-expressing HA-JIK and FLAG-JNK3 (lanes 3), but not phosphorylated when using a cell lysate prepared from cells expressing neither HA-JIK nor FLAG-JNK3 (lane 1) or cells expressing only FLAG-JNK3 (lanes 2).

Phosphorylated c-Jun increased in the kinase assay using a lysate of cells co-expressing HA-JIK and FLAG-JNK3 in comparison with the kinase assay using a lysate of cells expressing FLAG-JNK3 only, as shown in FIG. 8. Specifically, it was revealed that HA-JIK increases the c-Jun phosphorylation activity of JNK3.

The results obtained in the examples 6, 7 and 8 revealed that JIK binds to MKK7 and directly phosphorylates MKK7, which results in the activation of JNK3 followed by the phosphorylation of c-Jun, that is to say, the activation of JNK3 signaling pathway.

INDUSTRIAL APPLICABILITY

In the present invention, it was discovered for the first time that both PAK and JIK bind to MKK7, and that both PAK and JIK directly phosphorylate MKK7, and that as a result, the JNK3 signaling pathway is activated.

Although it has been already known that PAK4 activates the JNK signaling pathway, the mechanism thereof was unascertained. PAK4 is activated by cdc42. The activation of cdc42 gives rise to nerve cell death via the activation of the JNK signaling pathway. Therefore, the MKK7 phosphorylation by PAK4 is presumably involved in nerve cell death caused by the activation of the JNK3 signaling pathway.

Although it has been already reported that JIK is involved in the JNK activation caused by ER stress, the mechanism thereof was unascertained. ER stress gives rise to nerve cell death via the activation of the JNK signaling pathway. Therefore, the MKK7 phosphorylation by JIK is presumably involved in nerve cell death caused by the activation of the JNK3 signaling pathway.

Consequently, it is possible to inhibit the phosphorylation of c-Jun resulting from the activation of JNK3 signaling pathway by inhibiting the binding of PAK4 or JIK to MKK7, or the phosphorylation of MKK7 by PAK4 or JIK, and further to inhibit nerve cell death.

Since both PAK4 and JIK directly phosphorylate MKK7, PAK4 and JIK presumably phosphorylate MKK7 through different pathways, and therefore are both involved in the activation of the JNK3 signaling pathway. Therefore, to inhibit both the activation of MKK7 caused by PAK4 and that caused by JIK may provide a more enhanced effect in inhibiting the phosphorylation of c-Jun than to inhibit only the activation of MKK7 caused by either PAK4 or JIK.

The present invention is extremely useful for prevention and treatment of disorders caused by the activation of the JNK3 signaling pathway, such as disorders attributable to nerve cell death, more practically, neurodegenerative disorders; and also for the study of neurodegenerative disorders and the JNK signaling mechanism.

FREE TEXT in SEQUENCE LISTING

SEQ ID NO: 1: Partial sequence of MKK7, which is highly homologous to that (SEQ ID NO:3) of PAK4

SEQ ID NO: 2: Partial sequence of MKK7, which is highly homologous to that (SEQ ID NO:4) of PAK4

SEQ ID NO: 3: Partial sequence of PAK4, which is highly homologous to that (SEQ ID NO:1) of MKK7

SEQ ID NO: 4: Partial sequence of PAK4, which is highly homologous to that (SEQ ID NO:2) of MKK7

SEQ ID NO: 5: Partial sequence of MKK7, which is highly homologous to that (SEQ ID NO:7) of JIK SEQ ID NO: 6: Partial sequence of MKK7, which is highly homologous to that (SEQ ID NO:8) of JIK SEQ ID NO: 7: Partial sequence of JIK, which is highly homologous to that (SEQ ID NO:5) of MKK7

SEQ ID NO: 8: Partial sequence of JIK, which is highly homologous to that (SEQ ID NO:6) of MKK7

SEQ ID NO: 9: Partial sequence of MKK7, showing a high score in the local alignment between MKK7 and PAK4
SEQ ID NO: 10: Partial sequence of PAK4, showing a high score in the local alignment between MKK7 and PAK4
SEQ ID NO: 11: Partial sequence identical in the sequences of MKK7, PAK4 and JIK
SEQ ID NO: 12: Partial sequence of MKK7, showing a high score in the local alignment between MKK7 and PAK4
SEQ ID NO: 13: Partial sequence of PAK4, showing a high score in the local alignment between MKK7 and PAK4
SEQ ID NO: 14: Partial sequence of MKK7, showing a high score in the local alignment between MKK7 and PAK4
SEQ ID NO: 15: Partial sequence of PAK4, showing a high score in the local alignment between MKK7 and PAK4
SEQ ID NO: 16: Partial sequence identical in the sequences of MKK7 and PAK4
SEQ ID NO: 17: Partial sequence of MKK7, showing a high score in the local alignment between MKK7 and PAK4
SEQ ID NO: 18: Partial sequence of PAK4, showing a high score in the local alignment between MKK7 and PAK4
SEQ ID NO: 19: Partial sequence of MKK7, showing a high score in the local alignment between MKK7 and PAK4
SEQ ID NO: 20: Partial sequence of PAK4, showing a high score in the local alignment between MKK7 and PAK4
SEQ ID NO: 21: Partial sequence of MKK7, showing a high score in the local alignment between MKK7 and PAK4
SEQ ID NO: 22: Partial sequence of PAK4, showing a high score in the local alignment between MKK7 and PAK4
SEQ ID NO: 23: Partial sequence of MKK7, showing a high score in the local alignment between MKK7 and PAK4
SEQ ID NO: 24: Partial sequence of PAK4, showing a high score in the local alignment between MKK7 and PAK4
SEQ ID NO: 25: Partial sequence of MKK7, showing a high score in the local alignment between MKK7 and PAK4
SEQ ID NO: 26: Partial sequence of PAK4, showing a high score in the local alignment between MKK7 and PAK4
SEQ ID NO: 27: Partial sequence of MKK7, showing a high score in the local alignment between MKK7 and PAK4
SEQ ID NO: 28: Partial sequence of PAK4, showing a high score in the local alignment between MKK7 and PAK4
SEQ ID NO: 29: Partial sequence of MKK7, showing a high score in the local alignment between MKK7 and JIK
SEQ ID NO: 30: Partial sequence of JIK, showing a high score in the local alignment between MKK7 and JIK
SEQ ID NO: 31: Partial sequence of MKK7, showing a high score in the local alignment between MKK7 and JIK
SEQ ID NO: 32: Partial sequence of JIK, showing a high score in the local alignment between MKK7 and JIK
SEQ ID NO: 33: Partial sequence of MKK7, showing a high score in the local alignment between MKK7 and JIK
SEQ ID NO: 34: Partial sequence of JIK, showing a high score in the local alignment between MKK7 and JIK
SEQ ID NO: 35: Partial sequence of MKK7, showing a high score in the local alignment between MKK7 and JIK
SEQ ID NO: 36: Partial sequence of JIK, showing a high score in the local alignment between MKK7 and JIK
SEQ ID NO: 37: Partial sequence of MKK7, showing a high score in the local alignment between MKK7 and JIK
SEQ ID NO: 38: Partial sequence of JIK, showing a high score in the local alignment between MKK7 and JIK
SEQ ID NO: 39: Partial sequence of MKK7, showing a high score in the local alignment between MKK7 and JIK
SEQ ID NO: 40: Partial sequence of JIK, showing a high score in the local alignment between MKK7 and JIK
SEQ ID NO: 41: Partial sequence of MKK7, showing a high score in the local alignment between MKK7 and JIK
SEQ ID NO: 42: Partial sequence of JIK, showing a high score in the local alignment between MKK7 and JIK
SEQ ID NO: 43: Partial sequence of MKK7, showing a high score in the local alignment between MKK7 and JIK
SEQ ID NO: 44: Partial sequence of JIK, showing a high score in the local alignment between MKK7 and JIK
SEQ ID NO: 45: Partial sequence of MKK7, showing a high score in the local alignment between MKK7 and JIK
SEQ ID NO: 46: Partial sequence of JIK, showing a high score in the local alignment between MKK7 and JIK

What is claim is:

1. A method for identifying a compound that inhibits binding of p21-activated kinase 4 (PAK4) to MAP kinase kinase 7 (MKK7), comprising contacting PAK4 and/or MKK7 with AND WITHOUT A TEST COMPOUND a test compound under conditions that allow the binding of PAK4 to MKK7; and determining whether the test compound inhibits the binding of PAK4 to MKK7, by detecting the presence, absence or change of a signal generated by the binding of PAK4 to MKK7 IN THE PRESENCE AND ABSENCE OF A TEST COMPOUND.

* * * * *

SEQUENCE LISTING

```
<160> NUMBER OF SEQ ID NOS: 46

<210> SEQ ID NO 1
<211> LENGTH: 7
<212> TYPE: PRT
<213> ORGANISM: Homo sapiens
<220> FEATURE:
<221> NAME/KEY: MISC_FEATURE
<223> OTHER INFORMATION: Partial sequence of MKK7, which is highly
      homologous to that (SEQ ID NO:3) of PAK4

<400> SEQUENCE: 1

Asp Val Trp Ser Leu Gly Ile
1               5

<210> SEQ ID NO 2
<211> LENGTH: 6
<212> TYPE: PRT
<213> ORGANISM: Homo sapiens
<220> FEATURE:
<221> NAME/KEY: MISC_FEATURE
<223> OTHER INFORMATION: Partial sequence of MKK7, which is highly
      homologous to that (SEQ ID NO:4) of PAK4

<400> SEQUENCE: 2
```

-continued

```
Pro Pro Ala Arg Pro Arg
1               5

<210> SEQ ID NO 3
<211> LENGTH: 7
<212> TYPE: PRT
<213> ORGANISM: Homo sapiens
<220> FEATURE:
<221> NAME/KEY: MISC_FEATURE
<223> OTHER INFORMATION: Partial sequence of PAK4, which is highly
      homologous to that (SEQ ID NO:1) of MKK7

<400> SEQUENCE: 3

Asp Ile Trp Ser Leu Gly Ile
1               5

<210> SEQ ID NO 4
<211> LENGTH: 6
<212> TYPE: PRT
<213> ORGANISM: Homo sapiens
<220> FEATURE:
<221> NAME/KEY: MISC_FEATURE
<223> OTHER INFORMATION: Partial sequence of PAK4, which is highly
      homologous to that (SEQ ID NO:2) of MKK7

<400> SEQUENCE: 4

Pro Pro Ala Arg Ala Arg
1               5

<210> SEQ ID NO 5
<211> LENGTH: 6
<212> TYPE: PRT
<213> ORGANISM: Homo sapiens
<220> FEATURE:
<221> NAME/KEY: misc_feature
<223> OTHER INFORMATION: Partial sequence of MKK7, which is highly
      homologous to that (SEQ ID NO:7) of JIK

<400> SEQUENCE: 5

Trp Ser Leu Gly Ile Ser
1               5

<210> SEQ ID NO 6
<211> LENGTH: 6
<212> TYPE: PRT
<213> ORGANISM: Homo sapiens
<220> FEATURE:
<221> NAME/KEY: misc_feature
<223> OTHER INFORMATION: Partial sequence of MKK7, which is highly
      homologous to that (SEQ ID NO:8) of JIK

<400> SEQUENCE: 6

Leu Glu Ala Lys Leu Lys
1               5

<210> SEQ ID NO 7
<211> LENGTH: 6
<212> TYPE: PRT
<213> ORGANISM: Homo sapiens
<220> FEATURE:
<221> NAME/KEY: misc_feature
<223> OTHER INFORMATION: Partial sequence of JIK, which is highly
      homologous to that (SEQ ID NO:5) of MKK7

<400> SEQUENCE: 7

Trp Ser Leu Gly Ile Thr
1               5
```

```
<210> SEQ ID NO 8
<211> LENGTH: 6
<212> TYPE: PRT
<213> ORGANISM: Homo sapiens
<220> FEATURE:
<221> NAME/KEY: misc_feature
<223> OTHER INFORMATION: Partial sequence of JIK, which is highly
      homologous to that (SEQ ID NO:6) of MKK7

<400> SEQUENCE: 8

Leu Glu Asn Lys Leu Lys
1               5

<210> SEQ ID NO 9
<211> LENGTH: 24
<212> TYPE: PRT
<213> ORGANISM: Homo sapiens
<220> FEATURE:
<221> NAME/KEY: MISC_FEATURE
<223> OTHER INFORMATION: Partial sequence of MKK7, showing high score
      in the local alignment between MKK7 and PAK4

<400> SEQUENCE: 9

Tyr Asp Ile Arg Ala Asp Val Trp Ser Leu Gly Ile Ser Leu Val Glu
1               5                   10                  15

Leu Ala Thr Gly Gln Phe Pro Tyr
            20

<210> SEQ ID NO 10
<211> LENGTH: 24
<212> TYPE: PRT
<213> ORGANISM: Homo sapiens
<220> FEATURE:
<221> NAME/KEY: misc_feature
<223> OTHER INFORMATION: Partial sequence of PAK4, showing high score
      in the local alignment between MKK7 and PAK4

<400> SEQUENCE: 10

Tyr Gly Pro Glu Val Asp Ile Trp Ser Leu Gly Ile Met Val Ile Glu
1               5                   10                  15

Met Val Asp Gly Glu Pro Pro Tyr
            20

<210> SEQ ID NO 11
<211> LENGTH: 5
<212> TYPE: PRT
<213> ORGANISM: Homo sapiens
<220> FEATURE:
<221> NAME/KEY: misc_feature
<223> OTHER INFORMATION: Partial sequence identical in the sequences
      of MKK7, PAK4 and JIK

<400> SEQUENCE: 11

Trp Ser Leu Gly Ile
1               5

<210> SEQ ID NO 12
<211> LENGTH: 32
<212> TYPE: PRT
<213> ORGANISM: Homo sapiens
<220> FEATURE:
<221> NAME/KEY: MISC_FEATURE
<223> OTHER INFORMATION: Partial sequence of MKK7, showing high score
      in the local alignment between MKK7 and PAK4

<400> SEQUENCE: 12

Leu Glu Asn Leu Gly Glu Met Gly Ser Gly Thr Cys Gly Gln Val Trp
```

Lys Met Arg Phe Arg Lys Thr Gly His Val Ile Ala Val Lys Gln Met
            20                  25                  30

<210> SEQ ID NO 13
<211> LENGTH: 32
<212> TYPE: PRT
<213> ORGANISM: Homo sapiens
<220> FEATURE:
<221> NAME/KEY: misc_feature
<223> OTHER INFORMATION: Partial sequence of PAK4, showing high score
      in the local alignment between MKK7 and PAK4

<400> SEQUENCE: 13

Leu Asp Asn Phe Ile Lys Ile Gly Glu Gly Ser Thr Gly Ile Val Cys
1               5                   10                  15

Ile Ala Thr Val Arg Ser Ser Gly Lys Leu Val Ala Val Lys Lys Met
            20                  25                  30

<210> SEQ ID NO 14
<211> LENGTH: 14
<212> TYPE: PRT
<213> ORGANISM: Homo sapiens
<220> FEATURE:
<221> NAME/KEY: MISC_FEATURE
<223> OTHER INFORMATION: Partial sequence of MKK7, showing high score
      in the local alignment between MKK7 and PAK4

<400> SEQUENCE: 14

Pro Thr Pro Pro Ala Arg Pro Arg His Met Leu Gly Leu Pro
1               5                   10

<210> SEQ ID NO 15
<211> LENGTH: 14
<212> TYPE: PRT
<213> ORGANISM: Homo sapiens
<220> FEATURE:
<221> NAME/KEY: misc_feature
<223> OTHER INFORMATION: Partial sequence of PAK4, showing high score
      in the local alignment between MKK7 and PAK4

<400> SEQUENCE: 15

Pro Pro Pro Pro Ala Arg Ala Arg Gln Glu Asn Gly Met Pro
1               5                   10

<210> SEQ ID NO 16
<211> LENGTH: 4
<212> TYPE: PRT
<213> ORGANISM: Homo sapiens
<220> FEATURE:
<221> NAME/KEY: misc_feature
<223> OTHER INFORMATION: Partial sequence identical in the sequences
      of MKK7 and PAK4

<400> SEQUENCE: 16

Pro Pro Ala Arg
1

<210> SEQ ID NO 17
<211> LENGTH: 22
<212> TYPE: PRT
<213> ORGANISM: Homo sapiens
<220> FEATURE:
<221> NAME/KEY: misc_feature
<223> OTHER INFORMATION: Partial sequence of MKK7, showing high score
      in the local alignment between MKK7 and PAK4

<400> SEQUENCE: 17

```
Leu Thr Lys Asp His Arg Lys Arg Pro Lys Tyr Asn Lys Leu Leu Glu
1               5                   10                  15

His Ser Phe Ile Lys Arg
            20
```

<210> SEQ ID NO 18
<211> LENGTH: 22
<212> TYPE: PRT
<213> ORGANISM: Homo sapiens
<220> FEATURE:
<221> NAME/KEY: misc_feature
<223> OTHER INFORMATION: Partial sequence of PAK4, showing high score
      in the local alignment between MKK7 and PAK4

<400> SEQUENCE: 18

```
Leu Val Arg Asp Pro Ala Gln Arg Ala Thr Ala Ala Glu Leu Leu Lys
1               5                   10                  15

His Pro Phe Leu Ala Lys
            20
```

<210> SEQ ID NO 19
<211> LENGTH: 31
<212> TYPE: PRT
<213> ORGANISM: Homo sapiens
<220> FEATURE:
<221> NAME/KEY: misc_feature
<223> OTHER INFORMATION: Partial sequence of MKK7, showing high score
      in the local alignment between MKK7 and PAK4

<400> SEQUENCE: 19

```
Val Val Leu Lys Ser His Asp Cys Pro Tyr Ile Val Gln Cys Phe Gly
1               5                   10                  15

Thr Phe Ile Thr Asn Thr Asp Val Phe Ile Ala Met Glu Leu Met
            20                  25                  30
```

<210> SEQ ID NO 20
<211> LENGTH: 31
<212> TYPE: PRT
<213> ORGANISM: Homo sapiens
<220> FEATURE:
<221> NAME/KEY: misc_feature
<223> OTHER INFORMATION: Partial sequence of PAK4, showing high score
      in the local alignment between MKK7 and PAK4

<400> SEQUENCE: 20

```
Val Ile Met Arg Asp Tyr Gln His Glu Asn Val Val Glu Met Tyr Asn
1               5                   10                  15

Ser Tyr Leu Val Gly Asp Glu Leu Trp Val Val Met Glu Phe Leu
            20                  25                  30
```

<210> SEQ ID NO 21
<211> LENGTH: 33
<212> TYPE: PRT
<213> ORGANISM: Homo sapiens
<220> FEATURE:
<221> NAME/KEY: misc_feature
<223> OTHER INFORMATION: Partial sequence of MKK7, showing high score
      in the local alignment between MKK7 and PAK4

<400> SEQUENCE: 21

```
Asp Ile Ser Pro Gln Arg Pro Arg Pro Thr Leu Gln Leu Pro Leu Ala
1               5                   10                  15

Asn Asp Gly Gly Ser Arg Ser Pro Ser Ser Glu Ser Ser Pro Gln His
            20                  25                  30
```

Pro

<210> SEQ ID NO 22
<211> LENGTH: 34
<212> TYPE: PRT
<213> ORGANISM: Homo sapiens
<220> FEATURE:
<221> NAME/KEY: misc_feature
<223> OTHER INFORMATION: Partial sequence of PAK4, showing high score
      in the local alignment between MKK7 and PAK4

<400> SEQUENCE: 22

Asp Val Ala Pro Asn Gly Pro Ser Ala Gly Gly Leu Ala Ile Pro Gln
1               5                   10                  15

Ser Ser Ser Ser Ser Ser Arg Pro Pro Thr Arg Ala Arg Gly Ala Pro
            20                  25                  30

Ser Pro

<210> SEQ ID NO 23
<211> LENGTH: 15
<212> TYPE: PRT
<213> ORGANISM: Homo sapiens
<220> FEATURE:
<221> NAME/KEY: misc_feature
<223> OTHER INFORMATION: Partial sequence of MKK7, showing high score
      in the local alignment between MKK7 and PAK4

<400> SEQUENCE: 23

Ser Glu Ser Ser Pro Gln His Pro Thr Pro Pro Ala Arg Pro Arg
1               5                   10                  15

<210> SEQ ID NO 24
<211> LENGTH: 15
<212> TYPE: PRT
<213> ORGANISM: Homo sapiens
<220> FEATURE:
<221> NAME/KEY: misc_feature
<223> OTHER INFORMATION: Partial sequence of PAK4, showing high score
      in the local alignment between MKK7 and PAK4

<400> SEQUENCE: 24

Pro Gln Ser Ser Ser Ser Ser Ser Arg Pro Pro Thr Arg Ala Arg
1               5                   10                  15

<210> SEQ ID NO 25
<211> LENGTH: 20
<212> TYPE: PRT
<213> ORGANISM: Homo sapiens
<220> FEATURE:
<221> NAME/KEY: misc_feature
<223> OTHER INFORMATION: Partial sequence of MKK7, showing high score
      in the local alignment between MKK7 and PAK4

<400> SEQUENCE: 25

Gly Gly Ser Arg Ser Pro Ser Ser Glu Ser Ser Pro Gln His Pro Thr
1               5                   10                  15

Pro Pro Ala Arg
            20

<210> SEQ ID NO 26
<211> LENGTH: 20
<212> TYPE: PRT
<213> ORGANISM: Homo sapiens
<220> FEATURE:
<221> NAME/KEY: misc_feature
<223> OTHER INFORMATION: Partial sequence of PAK4, showing high score
      in the local alignment between MKK7 and PAK4

```
<400> SEQUENCE: 26

Gly Gly Leu Ala Ile Pro Gln Ser Ser Ser Ser Ser Arg Pro Pro
1               5                   10                  15

Thr Arg Ala Arg
            20

<210> SEQ ID NO 27
<211> LENGTH: 22
<212> TYPE: PRT
<213> ORGANISM: Homo sapiens
<220> FEATURE:
<221> NAME/KEY: misc_feature
<223> OTHER INFORMATION: Partial sequence of MKK7, showing high score
      in the local alignment between MKK7 and PAK4

<400> SEQUENCE: 27

Ile Ser Pro Gln Arg Pro Arg Pro Thr Leu Gln Leu Pro Leu Ala Asn
1               5                   10                  15

Asp Gly Gly Ser Arg Ser
            20

<210> SEQ ID NO 28
<211> LENGTH: 21
<212> TYPE: PRT
<213> ORGANISM: Homo sapiens
<220> FEATURE:
<221> NAME/KEY: misc_feature
<223> OTHER INFORMATION: Partial sequence of PAK4, showing high score
      in the local alignment between MKK7 and PAK4

<400> SEQUENCE: 28

Val Ser His Glu Gln Phe Arg Ala Ala Leu Gln Leu Val Val Asp Pro
1               5                   10                  15

Gly Asp Pro Arg Ser
            20

<210> SEQ ID NO 29
<211> LENGTH: 18
<212> TYPE: PRT
<213> ORGANISM: Homo sapiens
<220> FEATURE:
<221> NAME/KEY: misc_feature
<223> OTHER INFORMATION: Partial sequence of MKK7, showing high score
      in the local alignment between MKK7 and JIK

<400> SEQUENCE: 29

Tyr Asp Ile Arg Ala Asp Val Trp Ser Leu Gly Ile Ser Leu Val Glu
1               5                   10                  15

Leu Ala

<210> SEQ ID NO 30
<211> LENGTH: 18
<212> TYPE: PRT
<213> ORGANISM: Homo sapiens
<220> FEATURE:
<221> NAME/KEY: misc_feature
<223> OTHER INFORMATION: Partial sequence of JIK, showing high score
      in the local alignment between MKK7 and JIK

<400> SEQUENCE: 30

Tyr Asp Gly Lys Val Asp Ile Trp Ser Leu Gly Ile Thr Cys Ile Glu
1               5                   10                  15

Leu Ala
```

```
<210> SEQ ID NO 31
<211> LENGTH: 35
<212> TYPE: PRT
<213> ORGANISM: Homo sapiens
<220> FEATURE:
<221> NAME/KEY: misc_feature
<223> OTHER INFORMATION: Partial sequence of MKK7, showing high score
      in the local alignment between MKK7 and JIK

<400> SEQUENCE: 31

Leu Gly Glu Met Gly Ser Gly Thr Cys Gly Gln Val Trp Lys Met Arg
 1               5                  10                  15

Phe Arg Lys Thr Gly His Val Ile Ala Val Lys Gln Met Arg Arg Ser
            20                  25                  30

Gly Asn Lys
        35

<210> SEQ ID NO 32
<211> LENGTH: 35
<212> TYPE: PRT
<213> ORGANISM: Homo sapiens
<220> FEATURE:
<221> NAME/KEY: misc_feature
<223> OTHER INFORMATION: Partial sequence of JIK, showing high score
      in the local alignment between MKK7 and JIK

<400> SEQUENCE: 32

Leu His Glu Ile Gly His Gly Ser Phe Gly Ala Val Tyr Phe Ala Thr
 1               5                  10                  15

Asn Ala His Thr Ser Glu Val Val Ala Ile Lys Lys Met Ser Tyr Ser
            20                  25                  30

Gly Lys Gln
        35

<210> SEQ ID NO 33
<211> LENGTH: 22
<212> TYPE: PRT
<213> ORGANISM: Homo sapiens
<220> FEATURE:
<221> NAME/KEY: misc_feature
<223> OTHER INFORMATION: Partial sequence of MKK7, showing high score
      in the local alignment between MKK7 and JIK

<400> SEQUENCE: 33

Glu Gln Lys Leu Ser Arg Leu Glu Ala Lys Leu Lys Gln Glu Asn Arg
 1               5                  10                  15

Glu Ala Arg Arg Arg Ile
            20

<210> SEQ ID NO 34
<211> LENGTH: 22
<212> TYPE: PRT
<213> ORGANISM: Homo sapiens
<220> FEATURE:
<221> NAME/KEY: misc_feature
<223> OTHER INFORMATION: Partial sequence of JIK, showing high score
      in the local alignment between MKK7 and JIK

<400> SEQUENCE: 34

Gln Lys Gln Leu Ile Ala Leu Glu Asn Lys Leu Lys Ala Glu Met Asp
 1               5                  10                  15

Glu His Arg Leu Lys Leu
            20
```

```
<210> SEQ ID NO 35
<211> LENGTH: 16
<212> TYPE: PRT
<213> ORGANISM: Homo sapiens
<220> FEATURE:
<221> NAME/KEY: misc_feature
<223> OTHER INFORMATION: Partial sequence of MKK7, showing high score
      in the local alignment between MKK7 and JIK

<400> SEQUENCE: 35

Glu Ile Asp Gln Lys Leu Gln Glu Ile Met Lys Gln Thr Gly Tyr Leu
1               5                   10                  15

<210> SEQ ID NO 36
<211> LENGTH: 16
<212> TYPE: PRT
<213> ORGANISM: Homo sapiens
<220> FEATURE:
<221> NAME/KEY: misc_feature
<223> OTHER INFORMATION: Partial sequence of JIK, showing high score
      in the local alignment between MKK7 and JIK

<400> SEQUENCE: 36

Gln Thr His Glu Lys Trp Gln Asp Ile Leu Lys Glu Val Lys Phe Leu
1               5                   10                  15

<210> SEQ ID NO 37
<211> LENGTH: 19
<212> TYPE: PRT
<213> ORGANISM: Homo sapiens
<220> FEATURE:
<221> NAME/KEY: misc_feature
<223> OTHER INFORMATION: Partial sequence of MKK7, showing high score
      in the local alignment between MKK7 and JIK

<400> SEQUENCE: 37

Gln Thr Gly Tyr Leu Thr Ile Gly Gly Gln Arg Tyr Gln Ala Glu Ile
1               5                   10                  15

Asn Asp Leu

<210> SEQ ID NO 38
<211> LENGTH: 19
<212> TYPE: PRT
<213> ORGANISM: Homo sapiens
<220> FEATURE:
<221> NAME/KEY: misc_feature
<223> OTHER INFORMATION: Partial sequence of JIK, showing high score
      in the local alignment between MKK7 and JIK

<400> SEQUENCE: 38

Gln Thr Arg Lys Leu Ala Ile Leu Ala Glu Gln Tyr Glu Gln Ser Ile
1               5                   10                  15

Asn Glu Met

<210> SEQ ID NO 39
<211> LENGTH: 18
<212> TYPE: PRT
<213> ORGANISM: Homo sapiens
<220> FEATURE:
<221> NAME/KEY: misc_feature
<223> OTHER INFORMATION: Partial sequence of MKK7, showing high score
      in the local alignment between MKK7 and JIK

<400> SEQUENCE: 39

Leu Glu Gln Lys Leu Ser Arg Leu Glu Ala Lys Leu Lys Gln Glu Asn
1               5                   10                  15

Arg Glu
```

```
<210> SEQ ID NO 40
<211> LENGTH: 18
<212> TYPE: PRT
<213> ORGANISM: Homo sapiens
<220> FEATURE:
<221> NAME/KEY: misc_feature
<223> OTHER INFORMATION: Partial sequence of JIK, showing high score
      in the local alignment between MKK7 and JIK

<400> SEQUENCE: 40

Leu Glu Gln Arg Val Ser Leu Arg Arg Ala His Leu Glu Gln Lys Ile
1               5                   10                  15
Glu Glu

<210> SEQ ID NO 41
<211> LENGTH: 13
<212> TYPE: PRT
<213> ORGANISM: Homo sapiens
<220> FEATURE:
<221> NAME/KEY: misc_feature
<223> OTHER INFORMATION: Partial sequence of MKK7, showing high score
      in the local alignment between MKK7 and JIK

<400> SEQUENCE: 41

Gln Arg Tyr Gln Ala Glu Ile Asn Asp Leu Glu Asn Leu
1               5                   10

<210> SEQ ID NO 42
<211> LENGTH: 13
<212> TYPE: PRT
<213> ORGANISM: Homo sapiens
<220> FEATURE:
<221> NAME/KEY: misc_feature
<223> OTHER INFORMATION: Partial sequence of JIK, showing high score
      in the local alignment between MKK7 and JIK

<400> SEQUENCE: 42

Gln Arg Thr Lys Asp Ala Val Arg Glu Leu Asp Asn Leu
1               5                   10

<210> SEQ ID NO 43
<211> LENGTH: 10
<212> TYPE: PRT
<213> ORGANISM: Homo sapiens
<220> FEATURE:
<221> NAME/KEY: misc_feature
<223> OTHER INFORMATION: Partial sequence of MKK7, showing high score
      in the local alignment between MKK7 and JIK

<400> SEQUENCE: 43

Thr Cys Ala Glu Lys Leu Lys Lys Arg Met
1               5                   10

<210> SEQ ID NO 44
<211> LENGTH: 10
<212> TYPE: PRT
<213> ORGANISM: Homo sapiens
<220> FEATURE:
<221> NAME/KEY: misc_feature
<223> OTHER INFORMATION: Partial sequence of JIK, showing high score
      in the local alignment between MKK7 and JIK

<400> SEQUENCE: 44

Ile Cys Lys Glu Lys Ile Lys Glu Glu Met
1               5                   10
```

```
<210> SEQ ID NO 45
<211> LENGTH: 17
<212> TYPE: PRT
<213> ORGANISM: Homo sapiens
<220> FEATURE:
<221> NAME/KEY: misc_feature
<223> OTHER INFORMATION: Partial sequence of MKK7, showing high score
      in the local alignment between MKK7 and JIK

<400> SEQUENCE: 45

Lys His Gly Val Ile His Arg Asp Val Lys Pro Ser Asn Ile Leu Leu
1               5                   10                  15

Asp

<210> SEQ ID NO 46
<211> LENGTH: 16
<212> TYPE: PRT
<213> ORGANISM: Homo sapiens
<220> FEATURE:
<221> NAME/KEY: misc_feature
<223> OTHER INFORMATION: Partial sequence of JIK, showing high score
      in the local alignment between MKK7 and JIK

<400> SEQUENCE: 46

Arg His Asp Phe Val Arg Arg Asp Arg Pro Leu Arg Val Leu Ile Asp
1               5                   10                  15
```